United States Patent
Chiaramello et al.

(10) Patent No.: US 10,272,056 B2
(45) Date of Patent: Apr. 30, 2019

(54) TREATMENT FOR MITOCHONDRIAL DISEASES

(71) Applicant: The George Washington University a Congressionally Chartered Not-for-Profit Corporation, Washington, DC (US)

(72) Inventors: Anne Chiaramello, Washington, DC (US); Martine Uittenbogaard, Washington, DC (US)

(73) Assignee: The George Washington University, A Congressionally Chartered Not-for-Profit Corporation, Washington, DC (US)

( * ) Notice: Subject to any disclaimer, the term of this patent is extended or adjusted under 35 U.S.C. 154(b) by 0 days.

(21) Appl. No.: 15/548,233

(22) PCT Filed: Apr. 1, 2016

(86) PCT No.: PCT/US2016/025668
§ 371 (c)(1),
(2) Date: Aug. 2, 2017

(87) PCT Pub. No.: WO2016/161343
PCT Pub. Date: Oct. 6, 2016

(65) Prior Publication Data
US 2018/0263935 A1    Sep. 20, 2018

Related U.S. Application Data

(60) Provisional application No. 62/142,397, filed on Apr. 2, 2015.

(51) Int. Cl.
*A61K 31/19* (2006.01)
*A61K 31/225* (2006.01)
*A61P 25/00* (2006.01)
*G01N 33/50* (2006.01)

(52) U.S. Cl.
CPC ............ *A61K 31/19* (2013.01); *A61K 31/225* (2013.01); *A61P 25/00* (2018.01); *G01N 33/5079* (2013.01)

(58) Field of Classification Search
CPC .. A61K 31/19; A61K 31/225; G01N 33/5079; A61P 25/00
See application file for complete search history.

(56) References Cited

U.S. PATENT DOCUMENTS

2013/0123358 A1* 5/2013 Ye ..................... A61K 31/19
514/547

OTHER PUBLICATIONS

Ylikallio et al, Annals of Medicine, 44, 41-59 (Year: 2012).*
International Search Report and Written Opinion in International Application No. PCT/US2016/025668, dated Sep. 27, 2016.
Gallis et al., "Decrease in oxidative phosphorylation yield in presence of butyrate in perfused liver isolated from fed rats," BMC Physiology, vol. 7, No. 8, pp. 1-10 (2007).
McCarty, "Tributyrin may have practical potential for improving cognition in early alzheimer's disease via inhibition of HDAC2," pp. 1-7 (Sep. 2013).
Montague et al., "Screen for small molecules increasing the mitochondrial membrane potential," Journal of Biomolecular Screening, pp. 1-12 (2013).
Wang et al., "Butyrate activates the cAMP-protein kinase A-cAMP response element-binding protein signaling pathway in Caco-2 cells," The Journal of Nutrition, vol. 142, pp. 1-6 (2012).
Balbi, "Chloramphenicol: A Review," Pediatrics in Review, vol. 25, No. 8, pp. 284-287 (2004).
Gunning et al., "The Action of Nerve Growth Factor an Dibutyryl Adenosine Cyclic 3':5'—Monophosphate on Rat Pheochromocytoma Reveals Distinct Stages in the Mechanisms Underlying Neurite Outgrowth," The Journal of Neuroscience, vol. 1. No. 10, pp. 1085-1095 (1981).
Kaech et al., "Culturing hippocampal neurons," vol. 1., No. 5, Nature Protocols, pp. 2406-2415 (2006).
Lee et al., "Crucial roles of histone-modifying enzymes in mediating neural cell-type specification," Current Opinion in Neurobiology, 20:29-36 (2010).
Uittenbogaard et al., "Expression profiling upon Nex1/MATH-2-mediated neuritogenesis in PC12 cells and its implication in regeneration," Journal of Neurochemistry, vol. 91, pp. 1334-1343 (2004).
Uittenbogaard et al., "The neurogenic basic helix-loop-helix transcription factor NeuroD6 confers tolerance to oxidative stress by triggering an antioxidant response and sustaining the mitochondrial biomass," ASN Neuro 2(2): pp. 115-133 (2010).

* cited by examiner

*Primary Examiner* — Sudhakar Katakam
(74) *Attorney, Agent, or Firm* — Venable LLP; Henry J. Daley; Miguel A. Lopez

(57) ABSTRACT

The present application relates to methods of treating a subject with a disease or disorder associated with a mitochondrial deficit, comprising: determining at least one of a type or degree of the mitochondrial deficit in the subject; and administering an amount of a butyrate compound to the subject based at least partially on the determining step so as to promote Adenosine triphosphate (ATP) production in the subject as well as to methods of screening for compounds that restore cellular mitochondrial activity.

9 Claims, 17 Drawing Sheets

TREATMENT FOR MITOCHONDRIAL DISEASES

CROSS-REFERENCE OF RELATED APPLICATION

This application is a U.S. National Phase Application under 35 U.S.C. § 371 of PCT/US2016/025668 filed Apr. 1, 2016, which claims priority to U.S. Provisional Application No. 62/142,397 filed Apr. 2, 2015, the entire content of each of which is hereby incorporated by reference.

This invention was made with Government support under NINDS Grant Nos. R01NS041391 and R21NS085282 awarded by the National Institutes of Health (NIH). The U.S. Government has certain rights in the invention.

BACKGROUND

1. Field of Invention

The field of the currently claimed embodiments of this invention relate to methods of treating a subject with a disease or disorder associated with a mitochondrial deficit and methods of screening for compounds that restore cellular mitochondrial activity.

2. Discussion of Related Art

Mitochondrial diseases result from malfunction of the ubiquitous organelle, mitochondrion, which is responsible to generate ATP via the oxidative phosphorylation (OXPHOS) system. They are referred to as mitochondrial respiratory disorders (MRDs), which are incurable progressive degenerative diseases. Onset of these diseases varies from childhood to early adulthood. The two most frequent pediatric MRDs are MELAS (Mitochondrial Encephalopathy with Lactic Acidosis and Stroke-like episodes) and MERFF (Myoclonic Epilepsy with Ragged-Red Fibers). Patients exhibit heterogeneous clinical symptoms that include encephalopathy, seizures, stroke-like episodes, dementia, ataxia, migraine-like headaches, cognitive impairment, chronic lactic acidosis, cyclical vomiting, hypertrophic cardiomyopathy, myopathy, blindness, deafness, and diabetes. Currently, no therapeutic options are available to these patients, resulting in significant disability, a poor prognosis, and premature death. The devastation wrought by MRDs underscores the urgent need to develop therapeutic strategies.

MRDs, such as MELAS, are defined by insufficient ATP levels due to mutations in the mitochondrial genome or nuclear genome that affect the OXPHOS system. ATP is produced upon electron transfer through the first four OXPHOS complexes, with complexes I and II being the two points of entry for electrons and ATP synthesis occurring at complex V (FIG. 1). In MELAS, complex I is deficient, leading to insufficient ATP production. The MELAS mutation only affects a subset of the multi-copy mitochondrial genome, causing heteroplasmy. Most MELAS patients exhibit a maternally-inherited A to G substitution at position 3243 of the mitochondrial gene for tRNA$^{Leu(UUR)}$, known as the A3243G MELAS mutation, which mainly affects complex I due to its high leucine content. Although the prevalence of this disease is rare (1 in 15,000), the MELAS mutation has been detected in newborn cord bloods at the much higher frequency of 1 in 750. This difference stems from the variable ratios of mutant mtDNAs and wild type (WT) mtDNAs co-existing within cells, a state known as heteroplasmy. Individuals with the MELAS mutation become symptomatic only when the mutant load of diseased mitochondria exceeds a certain threshold (FIG. 2B).

MELAS patients display heteroplasmy at the organellar level (intra-mitochondrial heteroplasmy) and the cellular level (inter-mitochondrial heteroplasmy). Intra-mitochondrial heteroplasmy stems from the presence of both WT and mutant mtDNAs within a mitochondrion; this results in inter-mitochondrial heteroplasmy, a mixed population of healthy (functional) and diseased (dysfunctional) mitochondria (FIGS. 2A and 2B). A mitochondrion is considered diseased/dysfunctional if its mutant mtDNAs surpass a certain threshold, overwhelming its WT mtDNAs, and vice versa for healthy/functional mitochondria (FIG. 2A). Although the mechanism that progressively enriches the MELAS mutation remains largely unknown, emerging evidence suggests defective mitochondrial dynamics and turnover. In healthy cells, dynamic fusion-fission events lead to effective inter-mitochondrial exchange; this exchange "normalizes" the distribution of mutant mtDNAs among mitochondria with high mitochondrial membrane potential. In MELAS cells, diseased mitochondria are severely depolarized, which compromises inter-mitochondrial exchange via fusion, resulting in heteroplasmy (FIG. 2B). Moreover, ineffective clearance of diseased mitochondria via mitophagy further aggravates heteroplasmy over time in somatic cells. Recent data show that MELAS fibroblasts have a disrupted mitochondrial network with abundant fragmented and depolarized mitochondria, indicative of impaired fusion-fission events (FIG. 8).

SUMMARY

One embodiment of the invention includes a method of treating a subject with a disease or disorder associated with a mitochondrial deficit, comprising: determining at least one of a type or degree of said mitochondrial deficit in said subject; and administering an amount of a butyrate compound to said subject based at least partially on said determining so as to promote Adenosine triphosphate (ATP) production in said subject.

One embodiment of the invention includes a method of screening for a compound that restores cellular mitochondrial activity, comprising: culturing a cell; contacting said cell with a predetermined concentration or a predetermined range of concentrations of a compound of interest; collecting one or more of said cell or a byproduct of said cell and assaying said one or more of said cell or said byproduct of said cell for mitochondrial activity; and comparing said mitochondrial activity in said one or more of said cell or said byproduct of said cell to mitochondrial activity in a control sample, wherein an increase in mitochondrial activity in said one or more of said cell or said byproduct of said cell versus said mitochondrial activity in a control sample is indicative that said compound restores mitochondrial activity.

One embodiment of the invention includes a method of treating a subject with a disease or disorder associated with a mitochondrial deficit, comprising: administering an amount of a butyrate compound to said subject so as to promote Adenosine triphosphate (ATP) production in said subject.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figures 2A, 2B:
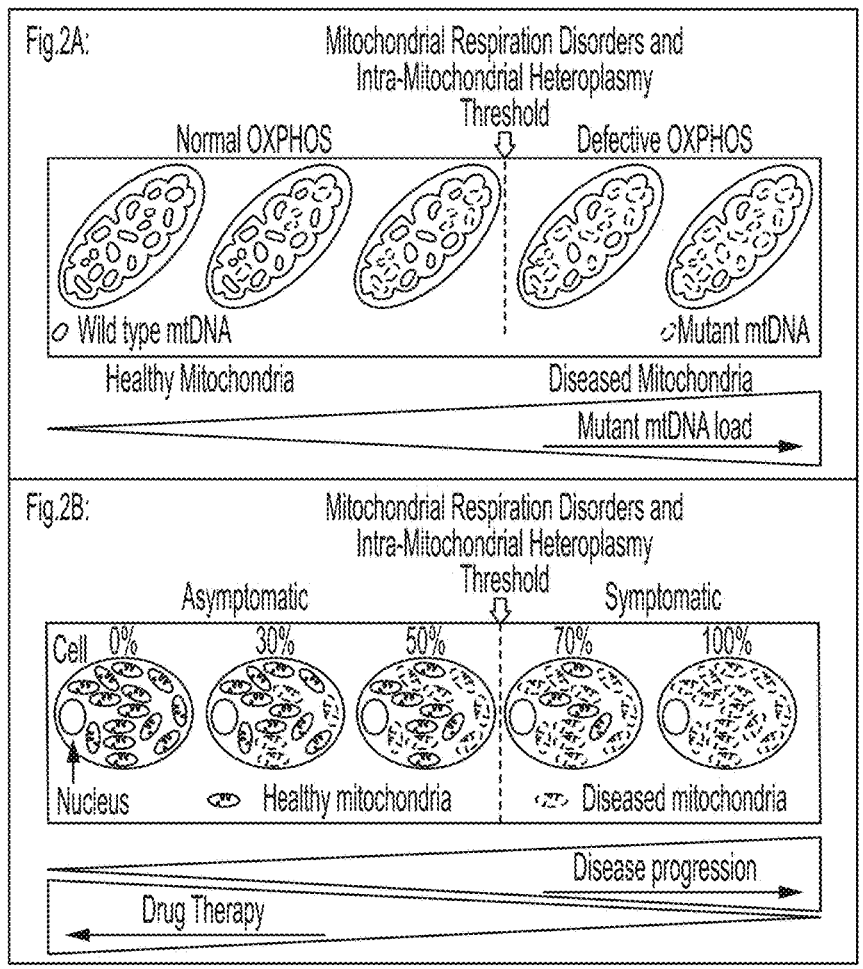
FIGS. 2A and 2B are a schematics showing mitochondrial respiratory disorders and intra-mitochondrial heteroplasmy.
Figure 8:
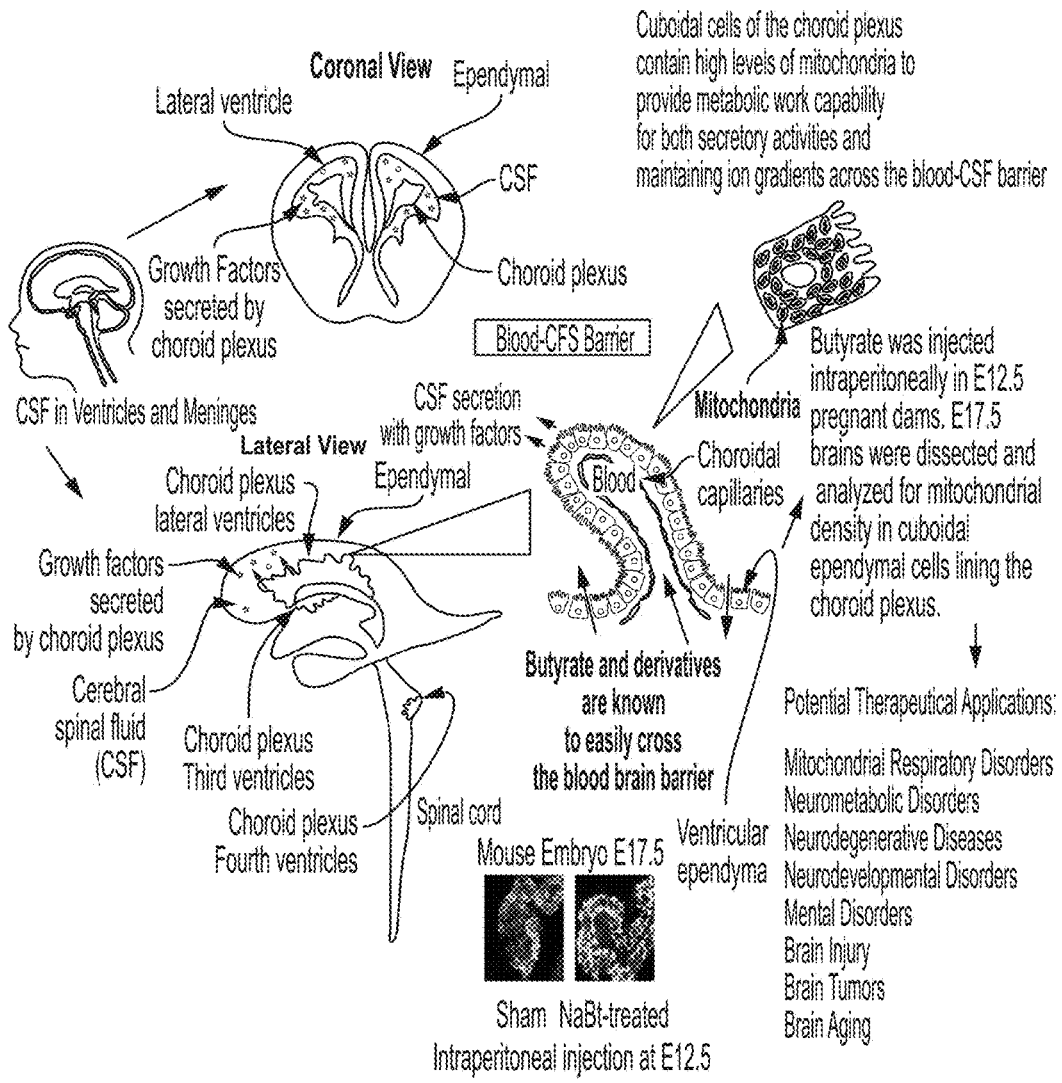
FIG. 8 is a schematic and image from microscopy showing that NaBt increases in vivo the mitochondrial mass of ependymal cells of the choroid plexus.

Some embodiments of the invention reduce the load of diseased mitochondria to a sub-threshold (FIG. 2B). A component of the studies described here aims to shift heteroplasmy toward healthy mitochondria by enhancing mitochondrial biogenesis. MELAS patients face a maladaptive response in skeletal muscle cells as well as endothelial and smooth muscle cells of small arteries that almost exclusively favors proliferation of diseased mitochondria. This response participates in the pathogenesis of stroke-like episodes in MELAS patients via an undetermined mechanism, possibly involving NO titration by increased COX IV activity in diseased mitochondria. Although the mechanism responsible for proliferation of diseased mitochondria remains elusive, it is known to bypass PGC-1α, the master regulator of mitochondrial biogenesis. PGC-1α interacts with key transcription factors, such as PPARs, NRF-1, and NRF-2, to stimulate nuclear gene expression and therefore mitochondrial biogenesis and OXPHOS activities. Currently, three approaches regulating the PGC1α pathway have proved insufficient: 1) gene therapy overexpressing PGC-1α improves the OXPHOS capacity in cybrid models and in skeletal muscle of animal models, but gene therapy for mitochondrial diseases is not yet feasible; 2) pharmacological use of the PGC-1α agonist bezafibrate had a limited effect on the mitochondrial mass in most mitochondrial encephalomyopathy mouse models due to insufficient induction of mitochondrial biogenesis; and 3) ketogenic diet boosts mitochondrial biogenesis and ATP levels in animal models and reduces the number of mutant mtDNAs in cybrid models, but it is too severe for long-term adherence by patients. In addition to this maladaptive response, MELAS fibroblasts have overall less mitochondrial mass than healthy fibroblasts (FIG. 8). Thus, in some embodiments, pharmacological agents that could mimic the ketogenic diet and boost biogenesis of functional mitochondrial mass we sought out.

Figure 1:
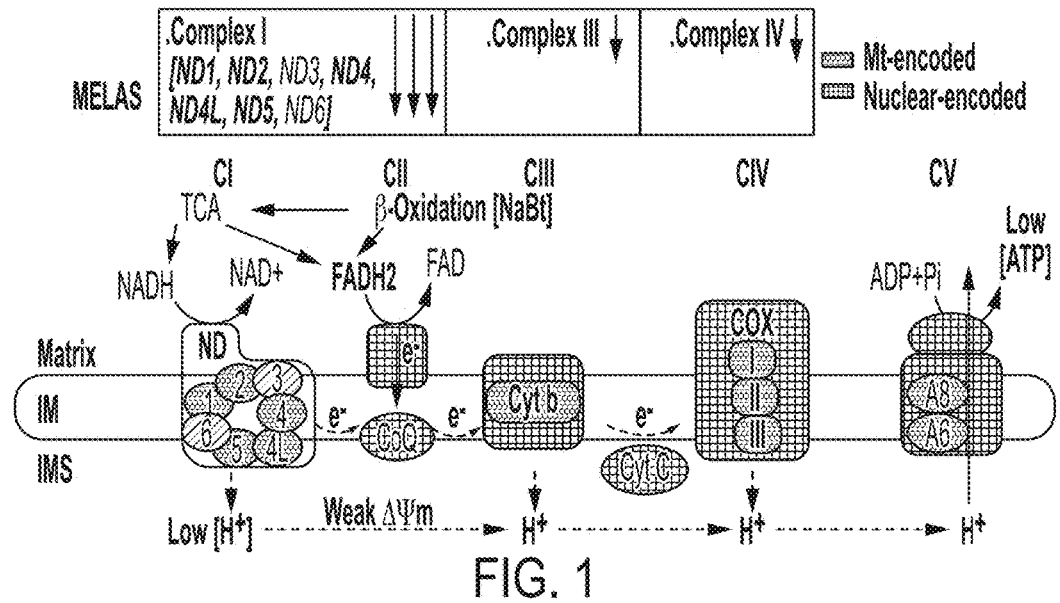
FIG. 1 is a schematic showing Mitochondrial Encephalopathy with Lactic Acidosis and Stroke-like episodes (MELAS) and oxidative phosphorylation (OXPHOS) system defects.
Figures 3A, 3B:
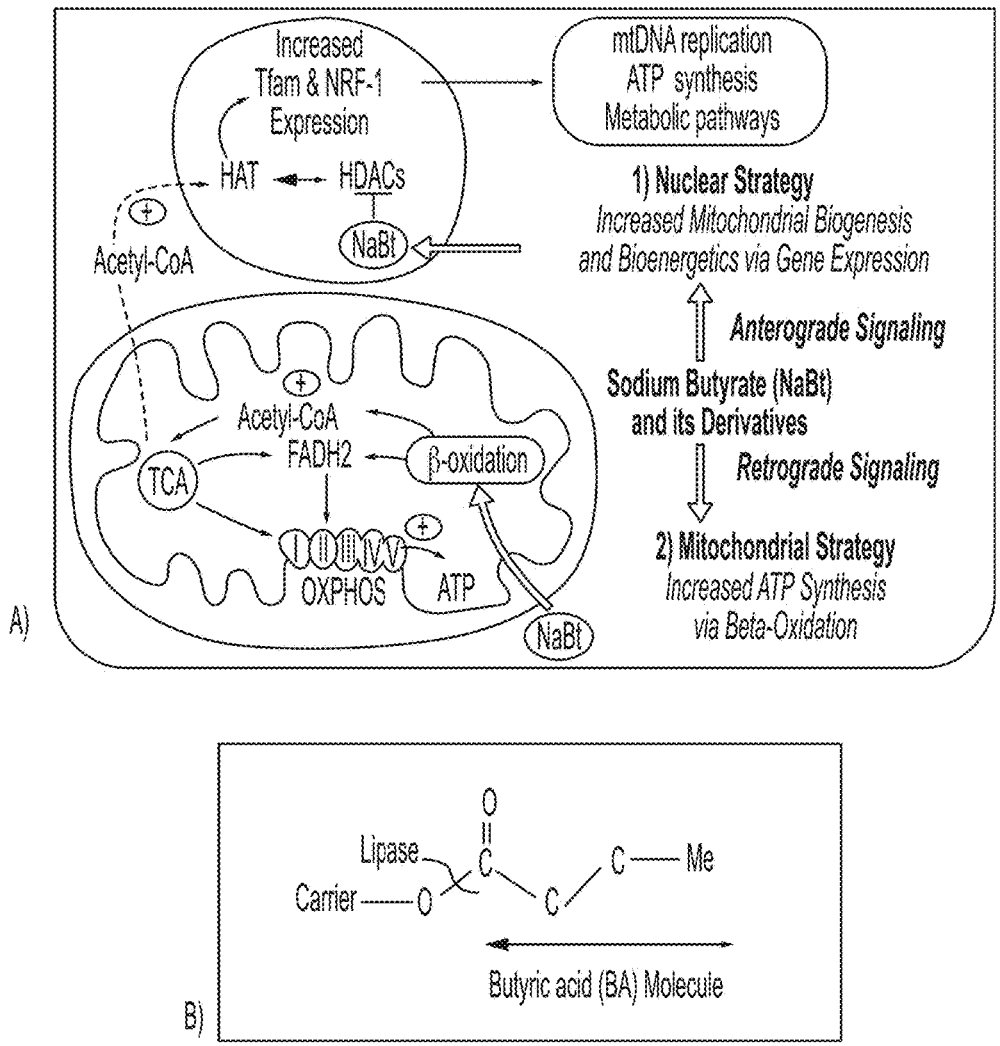
FIG. 3A is a schematic showing a pharmacological two pronged approach to remedy the ATP deficit associated with mitochondrial respiratory disorders.
FIG. 3B is a schematic showing the general structure of a Butyric Acid (BA) prodrug.

Some embodiments of the instant invention relate to a novel pharmaco-epigenomic strategy which takes advantage of the dual properties of butyrates. As short chain fatty acids, they can freely diffuse in mitochondria to boost ATP output, while as histone deacetylase inhibitors (HDACis), they act in the nucleus to modulate gene expression via histone acetylation (FIG. 3A). The novel pharmacological approach uses butyrates to promote nuclear and mitochondrial metabolic reprogramming for mitigating the chronic energy deficit in MELAS (FIG. 3A). Nuclear reprogramming increases mitochondrial biogenesis and therefore ATP levels, while mitochondrial metabolic reprogramming bypasses the defective complex I and enhances the activity of downstream complexes to boost ATP production (FIG. 1). The innovation aspect of the therapeutic approach is applicable to mitochondrial respiratory disorders (MRDs) and more broadly to diseases associated with mitochondrial dysfunction, such as neurodegenerative diseases, Duchenne's disease, cardiovascular diseases, stroke, metabolic disorders and renal diseases.

One embodiment of the invention includes a method of treating a subject with a disease or disorder associated with a mitochondrial deficit, comprising: determining at least one of a type or degree of said mitochondrial deficit in said subject; and administering an amount of a butyrate compound to said subject based at least partially on said determining so as to promote Adenosine triphosphate (ATP) production in said subject.

An embodiment of the invention relates to a method of treating a subject with a disease or disorder associated with a mitochondrial deficit comprising administering an amount of a butyrate compound resulting in synergizing a mitochondrial-nuclear crosstalk by promoting nuclear reprogramming and mitochondrial metabolic reprogramming.

An embodiment of the invention relates to a method of treating a subject with a disease or disorder associated with a mitochondrial deficit comprising administering an amount of a butyrate compound resulting in an increase in mitochondrial mass and biogenesis.

An embodiment of the invention relates to a method of treating a subject with a disease or disorder associated with a mitochondrial deficit comprising administering an amount of a butyrate compound resulting in increased mitochondrial membrane potential and bioenergetics.

An embodiment of the invention relates to a method of treating a subject with a disease or disorder associated with a mitochondrial deficit comprising administering an amount of a butyrate compound resulting in a decrease of diseased mitochondria.

An embodiment of the invention relates to a method of treating a subject with a disease or disorder associated with a mitochondrial deficit comprising administering a butyrate compound that is one or more of a synthetic butyric acid prodrug and a derivative of a synthetic butyric acid prodrug.

An embodiment of the invention relates to a method of treating a subject with a disease or disorder associated with a mitochondrial deficit comprising administering a butyrate compound selected from the group of butyrate compounds consisting of sodium butyrate, 1,3-Di(butanoyloxy)propan-2-yl butanoate and pivaloyloxymethyl butyrate.

An embodiment of the invention relates to a method of treating a subject with a disease or disorder associated with a mitochondrial deficit wherein said disease or disorder is a mitochondrial respiratory disorder, a neurodegenerative disease, a cardiovascular disease, a neurometabolic disorder, a muscular disorder, a metabolic disorder, or a renal disease.

An embodiment of the invention relates to a method of treating a subject with a disease or disorder associated with a mitochondrial deficit wherein said disease or disorder is a mitochondrial respiratory disorder.

An embodiment of the invention relates to a method of treating a subject with a disease or disorder associated with a mitochondrial deficit wherein said disease or disorder is Mitochondrial Encephalopathy with Lactic Acidosis and Stroke-like episodes (MELAS), Myoclonic Epilepsy with Ragged-Red Fibers (MERFF), or a mitochondrial respiratory disorder with a deficit in ATP levels due to a genetic mutation in a mitochondrial or nuclear genome.

An embodiment of the invention relates to a method of treating a subject with a disease or disorder associated with a mitochondrial deficit comprising administering a butyrate compound in an amount of about 150 mg/Kg/day to about 500 mg/Kg/day.

An embodiment of the invention relates to a method of treating a subject with a disease or disorder associated with a mitochondrial deficit comprising administering a butyrate compound for at least 3 days.

An embodiment of the invention relates to a method of treating a subject with a disease or disorder associated with a mitochondrial deficit comprising observing a resting period following administration of a butyrate compound and prior to administration of a subsequent dose of the butyrate compound.

An embodiment of the invention relates to a method of treating a subject with a disease or disorder associated with a mitochondrial deficit comprising administering a butyrate compound orally, intravenously, or by injection.

One embodiment of the invention includes a method of screening for a compound that restores cellular mitochondrial activity, comprising: culturing a cell; contacting said cell with a predetermined concentration or a predetermined range of concentrations of a compound of interest; collecting one or more of said cell or a byproduct of said cell and assaying said one or more of said cell or said byproduct of said cell for mitochondrial activity; and comparing said mitochondrial activity in said one or more of said cell or said byproduct of said cell to mitochondrial activity in a control sample, wherein an increase in mitochondrial activity in said one or more of said cell or said byproduct of said cell versus said mitochondrial activity in a control sample is indicative that said compound restores mitochondrial activity.

An embodiment of the invention relates to a method of screening for a compound that restores cellular mitochondrial activity in a cell, wherein said cell has decreased mitochondrial function.

An embodiment of the invention relates to a method of screening for a compound that restores cellular mitochondrial activity, comprising isolating a cell from a subject with a disease or disorder associated with a mitochondrial deficit prior to said culturing said cell.

An embodiment of the invention relates to a method of screening for a compound that restores cellular mitochondrial activity, comprising assaying one or more cells contacted with a test agent or a byproduct of said cells for mitochondrial activity comprises assaying for ATP production.

An embodiment of the invention relates to a method of screening for a compound that restores cellular mitochondrial activity, comprising assaying one or more cells contacted with a test agent or a byproduct of said cell for mitochondrial activity comprising assaying for nuclear reprogramming and mitochondrial metabolic reprogramming.

An embodiment of the invention relates to a method of screening for a compound that restores cellular mitochondrial activity, comprising assaying for mitochondrial biogenesis.

An embodiment of the invention relates to a method of screening for a compound that restores cellular mitochondrial activity, comprising assaying for mitochondrial metabolic reprogramming comprising assaying for mitochondrial potential.

An embodiment of the invention relates to a method of screening for a compound that restores cellular mitochondrial activity, wherein the compound of interest is a butyrate compound.

One embodiment of the invention includes a method of treating a subject with a disease or disorder associated with a mitochondrial deficit, comprising: administering an amount of a butyrate compound to said subject so as to promote Adenosine triphosphate (ATP) production in said subject.

Butyric Acid (BA) is a short chain fatty acid (SCFA) with the following properties: 1) it alters the epigenetic landscape of the nuclear genome by functioning as histone deacetylase inhibitors (HDACi) by favoring acetylation of histones, mainly H2B, H3 and H4. Consequently, this butyrate-induced epigenetic reprogramming results in a chromatin configuration permissive to gene expression; and 2) it is a short chain fatty acid (SCFA), capable to freely diffuse into the mitochondrial matrix, independent of any transporter activity. Once in the mitochondrial matrix, it undergoes fatty acid oxidation, which results in acetyl-CoA production (FIG. 3A; "Mitochondrial Strategy" arrow). Acetyl-CoA will serve as substrate for the tricarboxylic acid (TCA) cycle, also known as the Krebs cycle, producing NADH and FADH2, two electron donors for the oxidative phosphorylation (OXPHOS) system. Electrons enter the OXPHOS system at the level of complexes I and II to be transferred to the downstream OXPHOS complexes, resulting in ATP production at the last complex, complex V. Thus, fatty acid oxidation is another metabolic pathway to boost ATP levels.

Although the SCFA butyrate is well tolerated by humans with a low toxicity, its pharmokinetic properties, such as its short half-life, permeability and rapid metabolism, diminish its clinical effectiveness. This led to the design of synthetic butyrate (BA) prodrugs, such as Tributyrin (TBN) and AN-9 (also known as Pivanex), which contain a specific number of butyrate molecules. These prodrugs are pharmacologically inactive molecules, which require intracellular lipases to release the pharmacologically active butyric acid molecules from the prodrug molecule. FIG. 3B is a schematic showing the general structure of BA prodrugs. Upon cleavage, TBN releases three BA molecule, while AN-9 releases one BA molecules. They both display low toxicity with improved pharmacokinetic and pharmacodynamics properties, resulting in higher potency and longer half-life and cellular permeability than butyric acid.

What differs among the BA prodrugs is their "carrier" moieties, which are designed to possess minimal toxicity upon cleavage by specific lipases and resistance to the digestive tract. The ideal BA drugs should be cleaved by hepatic lipases instead of intestinal lipases to maximize their potency and efficacy. For example, the carrier moieties are either acidic (AN-40, AN-90, AN-96, AN-47), basic (AN-41, AN-46, AN-85) or neutral (AN-9, AN-1, AN-2, AN-7, AN-10, AN-11; AN-88, AN-42, AN-48). However, this is not by far a comprehensive list of all the BA prodrugs synthesized to date. To date, only AN-9 is available for researchers from commercial biotech companies, such as Sigma Aldrich. Another critical difference among BA prodrugs is their drug loading capacity, which is dictated by the drug to carrier ratio thereby modulating the number of butyrate molecules released upon cleavage by specific lipase enzymes.

Some embodiments of the invention include a method of treating a human subject with a disease or disorder associated with a mitochondrial deficit, comprising: administering an amount of a butyrate compound to the human subject so as to promote Adenosine triphosphate (ATP) production in the human subject. In such embodiments, the butyrate compound is administered in an amount of at least about 1 mg/Kg/day to about 50 mg/Kg/day to reach butyrate concentrations of 50 100 μM in human plasma. In other embodiments, the butyrate compound is administered in an amount of about 150 mg/Kg/day to about 500 mg/Kg/day, or between 150 and 350 mg/kg/day with an increment of about 50 mg/kg/day. In some instances, this dose is increased up to 750 mg/kg/day. In addition, the compound is administered for at least 3 days. This initial administration is, in some cases, followed by a resting period of two weeks wherein the compound is not administered to the human subject prior to further or additional administration of the compound.

It is within the skill of one of ordinary skill in the art to envision that various BA prodrugs can be used in place of or in combination with those described here. In addition, should the dose limiting toxicity of a specific butyrate compound not be reached at the highest does, the protocol may be adjusted to permit higher doses.

In some embodiments, a step of determining at least one of a type or degree of a mitochondrial deficit in a subject is carried out. In such a step, determining can be done in a number of ways available in a clinical or laboratory setting. Such tests or assays are known to one of ordinary skill in the art. Diagnostic tests for such defects include but are not limited to: muscle biopsy, blood enzyme tests, genetic tests, various assays for mitochondrial function, assays for biochemical activity and/or ATP production of cells or tissues, evaluation of multiple symptoms (e.g. muscle weakness, exercise intolerance, hearing impairment, ataxia, seizures, learning disabilities, cataracts, heart defects, diabetes and stunted growth), a physical exam including tests of strength and/or endurance, tests/biopsies of organs and/or tissues including brain, liver and/or muscle, or various non-invasive techniques including but not limited to phosphorus magnetic resonance spectroscopy, Computerized Tomography scans, Magnetic Resonance Imaging scans, electroencephalogram, and electrocardiogram.

The following examples describe some embodiments and some applications in more detail. However, the broad concepts of the current invention are not limited to the particular examples.

EXAMPLES

Example 1

Experimental Approach:
Pharmaco-epigenomic agents. Butyrates are naturally produced in the colon at high concentration (20 mM) where they epigenetically modulate energy metabolism. Despite their potency in the mM range, butyrates display low toxicity in contrast to the high toxicity of hydroxamate-based HDACis, even in their nM range. Here, it is described that hydroxamates trichostatin A and vorinostat induce apoptosis of MELAS fibroblasts. The butyrates TBN and AN9 display enhanced potency due to improved delivery efficiency and the number of butyric acid molecules upon cleavage by intracellular lipases. AN9, which acts faster than NaBt, exhibits low toxicity, increased cell membrane permeability, and intracellular delivery of butyric acid molecules. Due to its enhanced in vivo potency in the µM range, AN9 is orally administered with low toxicity at pharmacological concentrations 140 times lower than NaBt. TBN is more potent than NaBt due to its cleavage into three molecules of butyric acid. A concentration up to 2 mM of TBN is pharmacologically attainable via oral administration without toxicity or side effects. Butyrates easily cross the blood-brain barrier and induce differentiation of embryonic or adult progenitors into neurons through the NeuroD members, such as NeuroD6. In mouse models of neurodegenerative diseases and ischemia/stroke, NaBt stimulates neurogenesis, enhances synaptic plasticity and memory, while preventing neuronal death—processes in which mitochondria play a crucial role. This is particularly relevant given the symptoms of stroke-like episodes, seizures, and dementia in MELAS patients.

Experimental paradigms. These are: 1) E17.5 differentiating hippocampal neurons expressing NeuroD6; 2) the PC12-NeuroD6 neuronal cell line recapitulating the early stages of differentiation; 3) E12.5 timed-pregnant dams treated intraperitoneally with NaBt (1.2 g/Kg) or PBS; and 4) cultured primary skin fibroblasts isolated from two MELAS patients and a healthy subject. Patient fibroblasts are the most suitable system to investigate the therapeutic potential of the butyrate derivatives (NaBt, TBN, and AN9) within the context of the patient's nuclear background and heteroplasmy, as MELAS animal models have not been generated due to polyploidy of the mt genome, heteroplasmic load, and influence of the nuclear background on MELAS phenotypic variability. The other advantage of the ex-vivo cellular system described here, dermal fibroblasts derived from patients, lies in the reprogramming to induced-pluripotent stem cells for differentiation into somatic cells for testing our pharmacological approach.

Experimental approaches. Five distinct molecular tools were used to investigate mitochondrial biogenesis: 1) the mitochondrial-specific dyes, MitoTracker® Green (MTG) and MitoTracker® Red (MTR); 2) the mito-GFP or mito-dsRed vector to fluorescently label mitochondria; 3) antibodies against mtDNA, COXVα, or SOD2; 4) the fluorescent PicoGreen® dye labeling mtDNA; and 5) quantitative PCR to determine mtDNA copy number. Dose-dependent studies were performed on healthy and MELAS fibroblasts to determine the optimal safe concentrations of NaBt (2.5 mM), TBN (1.5 mM), and AN9 (300 µM) for eliciting maximal mitochondrial biogenesis without cellular toxicity after three days of treatment.

Figures 4A, 4B, 4C, 4D, 4E:
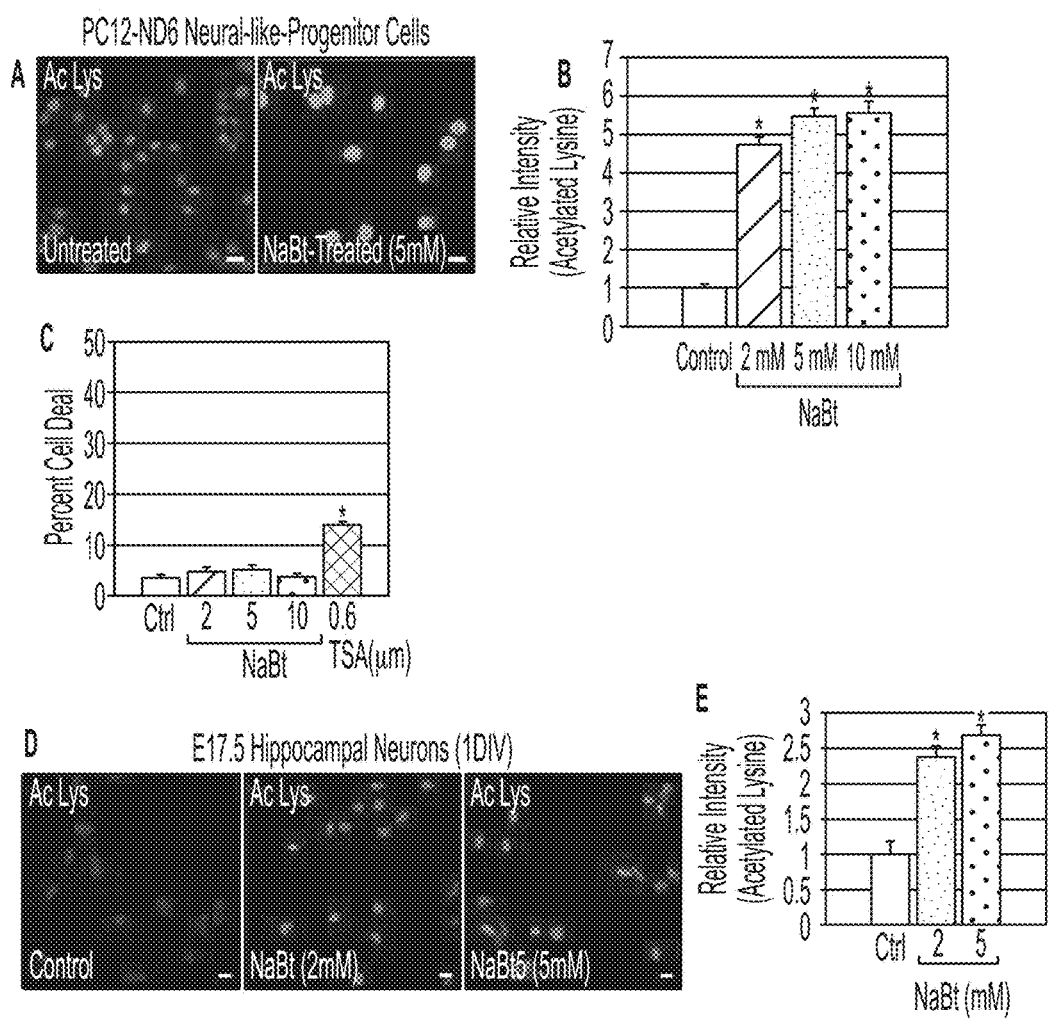
FIG. 4A-4E are images from microscopy and graphs showing NaBt dose-dependent acetylation and cellular toxicity in PC12-ND6 cells and embryonic E17.5 hippocampal neurons. (A) Confocal micrographs of PC12-ND6 cells (referred to as ND6) grown in the absence or presence of NaBt for three days and labeled with an anti-acetylated Lys antibody (AcLys; green). Scale bar represents 10 μm. (B) The graph shows the quantification of the NaBt concentration-dependent acetylation of nuclear proteins in untreated (control) and NaBt-treated PC12-ND6 cells. Results are expressed as relative fluorescence intensity±S.D. (n=250 cells per NaBt concentration; * p=0.0001). (C) Effect of NaBt on PC12-ND6 cell viability. As a control, PC12-ND6 cells were treated with the HDAC inhibitor TSA (0.66 μM) known to induce mild cell death. Mean±SEM (n=250 cells for each experimental condition; * p=0.0001). (D) Confocal micrographs of NaBt dose-dependent acetylation in E17.5 hippocampal neurons (AcLys; green). Scale bar represents 10 μm. (E) The graph shows the corresponding quantification analysis with results expressed as relative fluorescence intensity±S.D. (n=250 cells per NaBt concentration; *p=0.0001).

Results:

Sodium butyrate increases protein acetylation in a dose-dependent manner without inducing cellular toxicity. A dose response analysis was performed to determine the optimal concentration of sodium butyrate (NaBt) for inducing maximal acetylation levels with minimal cellular toxicity. PC12-ND6 cells were treated with different concentrations of NaBt (2 mM, 5 mM, and 10 mM) for three days before assessing the degree of acetylated lysine residues by immunocytochemistry and cell viability by live-cell confocal microscopy using the Nuclear-ID™ stain. Quantification analysis of the NaBt dose-dependent assay showed maximal acetylation levels of nuclear proteins in the presence of 5 mM NaBt with negligible cell death (FIG. 4A-C). Similarly, exposure of E17.5 hippocampal neurons at 1DIV to the HDACi NaBt resulted in increased acetylation levels of nuclear proteins in a concentration-dependent manner, with a 2 mM concentration of NaBt resulting in near maximal acetylation levels without affecting cellular viability (FIGS. 4D and E).

Figure 5:
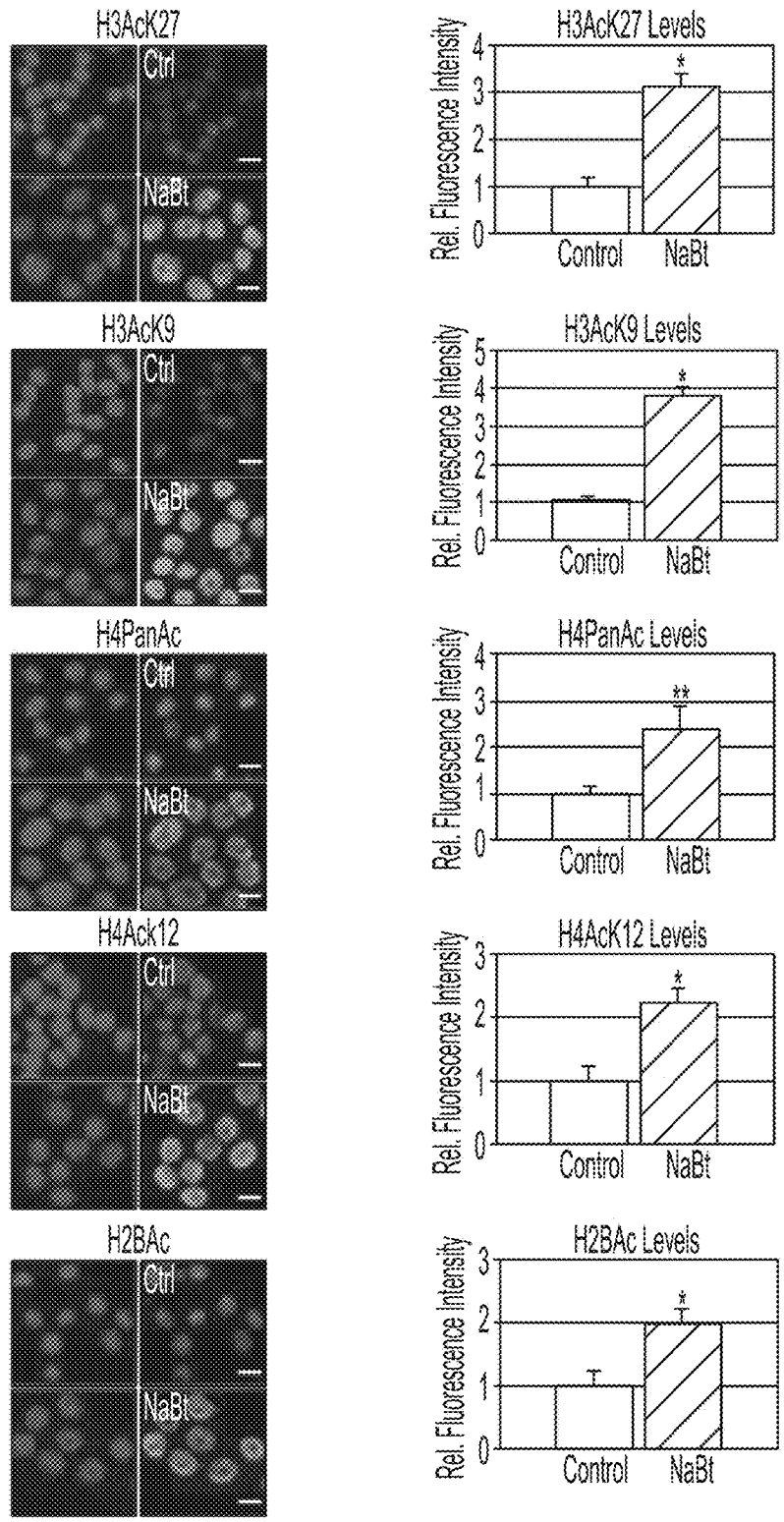
FIG. 5 shows images from microscopy and graphs showing NaBt induces chromatin remodeling by acetylating specific residues of histones H2B, H3 and H4 proteins. PC12-ND 6 cells were treated with NaBt (5 mM) for three days before performing immunocytochemistry to evaluate the acetylation status of lysine residues of key histone proteins, as listed on top of each confocal micrograph. Left panels illustrate representative pictures of PC12-ND6 cells grown in the absence (control) or presence of NaBt for three days and labeled with specific acetylated Lys antibody (green) and DAPI as a nuclear label (blue). Scale bar represents 10 μm. The right panels show the graph for each quantification of acetylated lysine residue for key histone proteins. Results are expressed as relative fluorescence intensity±S.D. (1000 cells per condition; n=3; * p=0.0001).

Sodium butyrate induces epigenetic reprogramming by acetylating key amino acid residues of histone proteins H2B, H3 and H4. Histone acetylation, which is mediated by two groups of enzymes, histone acetyltransferases (HATs) and histone deacetylases (HDAC), promote gene expression responsible to induce differentiation of neural stem cells and neural progenitor cells. Epigenetic regulators, such as the NaBt and its derivatives, inhibit the activity of HDAC enzymes, thereby favoring HAT activity and inducing an open chromatin structure to allow easy access to the DNA via histone acetylation. Thus, which lysine residues of key histone proteins were targeted by NaBt ws investigated. The lysine residue K27 of the histone H3 protein was targeted, as it is known to be acetylated to favor expression of lineage-specific genes associated with neural differentiation of progenitors and stem cells. Immunocytochemistry results confirmed that NaBt induced a 210% increased acetylation of the K27 residue of H3 (FIG. 5). Analysis was extended to additional acetylation marks, such as the lysine residue K9 of the histone H3, the K12 residue of histone H4 and, as they are important indicators of active enhancer elements. The results show that NaBt increased acetylation of H3K9 and H4K12 by 250% and 124%, respectively (FIG. 5). It was also found that NaBt hyperacetylated the histone H2B (FIG. 5), which functions as an active mark for an open chromatin mark. Thus, NaBt induces a specific epigenetic reprogramming of neural-like progenitor PC12-ND6 cell by inducing a series of acetylation marks to confer transcriptional competence.

Figure 6:
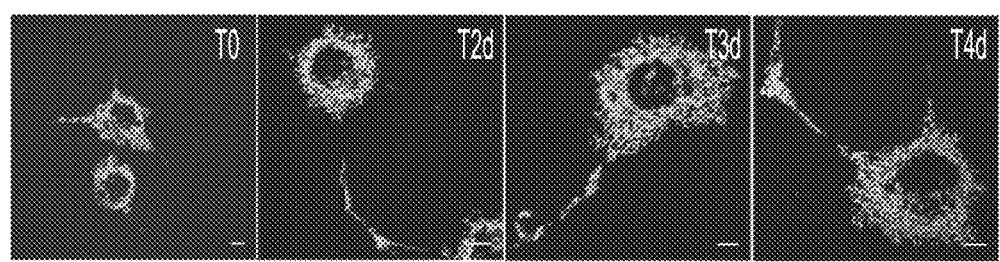
FIG. 6 shows images from microscopy showing NaBt induces maximal increase of the mitochondrial biomass after three days of treatment. PC12-ND6 cells were transfected with the mito-GFP vector prior to treatment with NaBt (5 mM) for the indicated time points. Mitochondria were visualized by live cell microscopy; scale bar=5 μm.

NaBt increases the mitochondrial biomass of neuronal cells in vitro and in vivo. To investigate the effect of NaBt on mitochondrial mass, PC12-ND6 cells were transfected with the mito-GFP vector before performing a time course analysis of NaBt (5 mM) treatment. Maximal increase of the mitochondrial biomass was observed after three days of NaBt exposure (FIG. 6).

Figures 7A, 7B, 7C, 7D, 7E, 7F:
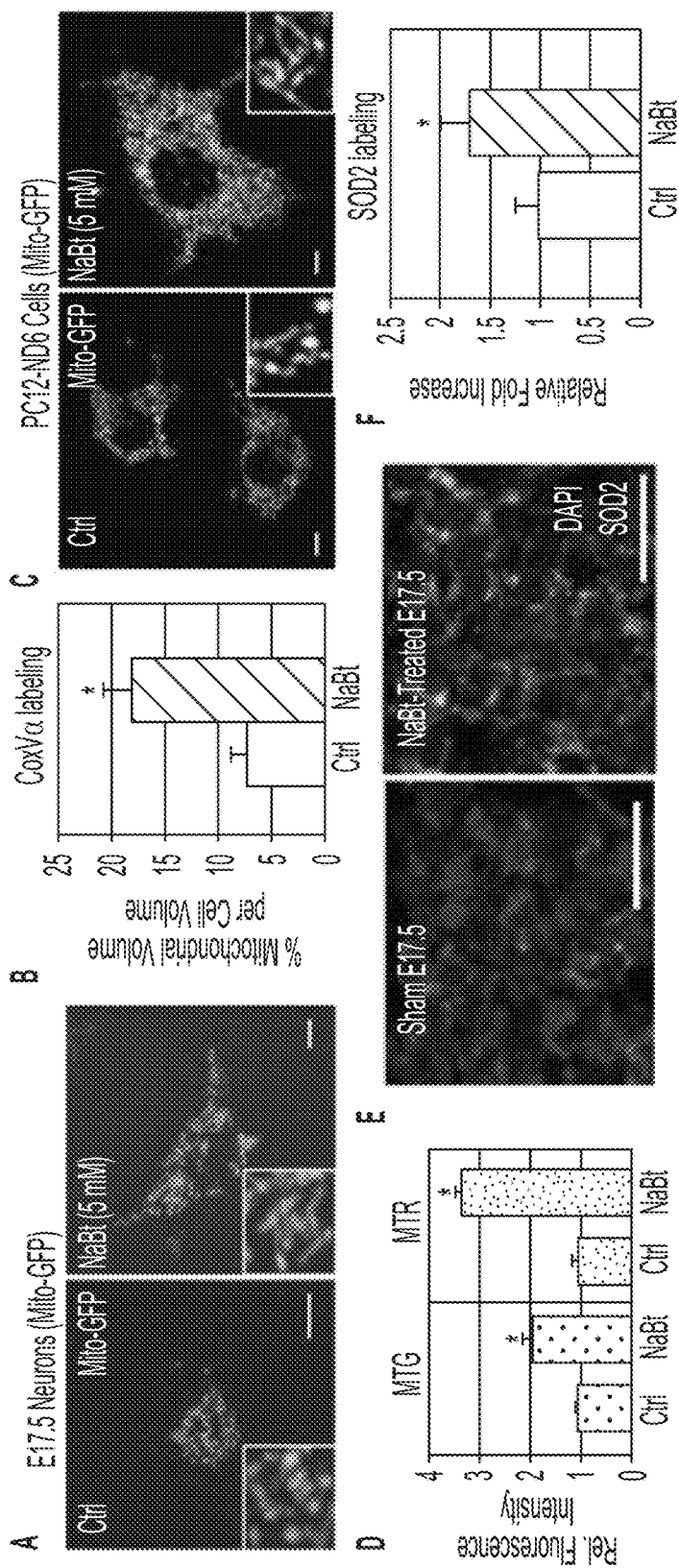
FIG. 7A-7F show images from microscopy and graphs showing NaBt increases mitochondrial mass. (A) Live cell confocal microscopy of E17.5 hippocampal neurons; high magnification in inset; scale bar=5 (B) Quantitative analysis of the mitochondrial biomass in E17.5 neurons using an anti-CoxVα antibody; *p<0.001. (C) Live cell confocal microscopy of PC12-ND6 cells; high magnification in inset; scale bar=5 (D) Flow cytometric analysis of mitochondrial mass; *p<0.001. (E) Confocal microscopy of E17.5 brains from E12.5 pregnant dams treated with PBS (sham) or NaBt; scale bar=20 (F) Quantitative analysis of mitochondrial mass; *p<0.001.

The effect of NaBt was investigated in embryonic neuronal progenitor cells, E17.5 hippocampal neurons, which were transfected with the mito-GFP vector and then exposed to various concentrations of NaBt. A similar increase in mitochondrial mass upon exposure to either 2 mM or 5 mM of NaBt was observed. Therefore, all subsequent treatment of E17.5 hippocampal neurons with NaBt was performed in the presence of 2 mM. However, both types of neuronal cells showed increased mitochondrial mass upon NaBt exposure (FIG. 7A, C). Quantitative immunohistochemistry using stacked confocal images and antibodies against COXVα and tubulin revealed mitochondria making up 7% of the cell volume in control and 18% in NaBt-treated E17.5 neurons (FIG. 7B). Flow cytometric analysis using MTG- or MTR-labeled cells corroborated the NaBt-mediated increase in mitochondrial mass (FIG. 7D). While MTG staining showed a two-fold increase in mitochondrial mass, MTR staining revealed an accentuated increase in fluorescence intensity (3.5-fold), suggesting enhanced mitochondrial membrane potential ($\Delta_{\psi m}$) in keeping with the elongated mitochondrial morphology characteristics of bioenergetic mitochondria (FIG. 7A, C, D). Using E12.5 pregnant dams treated intraperitoneally with NaBt or PBS, we found that NaBt increased the in vivo mitochondrial mass of E17.5 neurons 1.6-fold (FIGS. 7E and F).

NaBt increases in vivo the mitochondrial mass of ependymal cells of the choroid plexus. NaBt's effect on mitochondrial mass of ependymal cells from the choroid plexus was investigated. It is a highly vascularized tissue lining the brain ventricles, which is responsible for producing and secreting the cerebral spinal fluid (CSF) and for supplying growth factors and key ions to the developing and mature brain (FIG. 7). The secretory functions of the ependymal cells are highly dependent of mitochondria to ensure active transports of small ions, water and growth factors from the blood side to the CSF side. Impairment of mitochondrial functions in the choroid plexus has been documented in neurodegenerative diseases, such as Alzheimer's disease. To test the effect of NaBt in the choroid plexus of the murine developing brain, NaBt was injected intraperitoneally in E12.5 pregnant dams before dissected the brains at E17.5. Immunohistochemistry was performed on E17.5 sectioned brains to analyze the mitochondrial mass using an antibody against the mitochondrial marker SOD2. A substantial increase in the mitochondrial mass of the ependymal cells of the choroid plexus upon exposure to NaBt was observed, when compared to that of E17.5 ependymal cells from sham-intraperitoneally treated mice (FIG. 8).

Therefore, the butyrate results support the rationale for a novel pharmacological choroid plexus-based therapeutic strategy for nervous system repairs in the case of mitochondrial respiratory disorders, neurodegenerative diseases, neurodevelopmental disorders, and brain injury (FIG. 8). This is particularly relevant for the MELAS disease, as patients harbor diseased mitochondria in the ependymal cells of the choroid plexus.

Figures 9A, 9B, 9C:
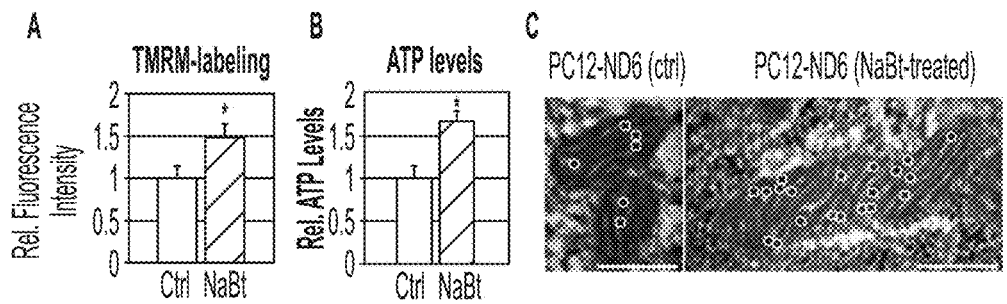
FIG. 9A-9C are graphs and images from microscopy showing that NaBt enhances mitochondrial bioenergetics. (A) Flow cytometric analysis of $\Delta_{\psi m}$; *p<0.001. (B) ATP levels in live cells using a $Mg^{2+}$-based assay; *p<0.001. (C) Electron microscopy of mitochondria in control and NaBt-treated cells; scale bar=200 nm.

NaBt increases mitochondrial membrane potential ($\Delta_{\psi m}$) and ATP levels. The MTR-based data raised the question: could NaBt also enhance mitochondrial bioenergetics? $\Delta_{\psi m}$ was assessed by live cell confocal microscopy and flow cytometry using the TMRM dye, which accumulates in the mitochondrial matrix in a $\Delta_{\psi m}$-dependent fashion. A 1.5-fold increase in $\Delta_{\psi m}$ in NaBt-treated cells was observed (FIG. 9A). To test whether enhanced $\Delta_{\psi m}$ led to increased ATP output, ATP levels were monitored using the live cell $Mg^{2+}$-based ATP assay, which is compatible with the TMRM dye, allowing simultaneous recordings. A 1.6-fold increase in ATP levels in NaBt-treated cells was observed (FIG. 9B), in line with the MTR- and TMRM-based findings and the elongated mitochondrial morphology. Electron microscopy confirmed this micro-architectural change with increased numbers of elongated cristae carrying the OXPHOS system and mtDNA foci, indicating enhanced bioenergetic capacity, mitochondrial biogenesis, and mtDNA replication (FIG. 9C).

Figure 10:
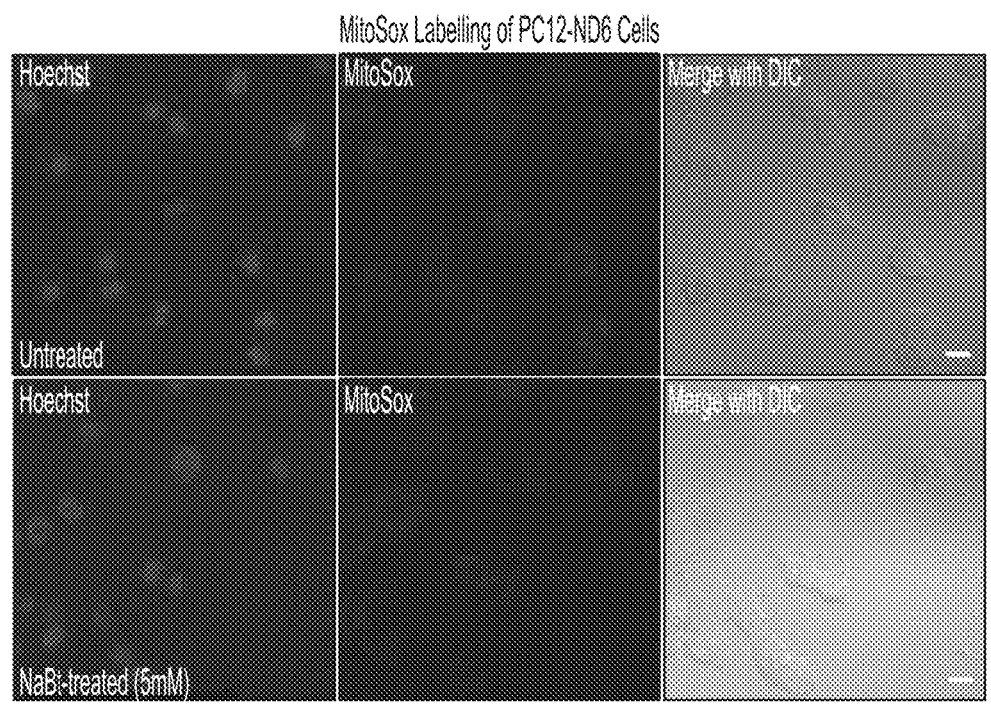
FIG. 10 shows images from microscopy showing treatment of PC12-ND6 cells with NaBt does not trigger ROS generation. PC12-ND6 cells were grown in the absence or presence of NaBt (5 mM) for three days before being labeled with the MitoSox™ dye and the nuclear counterstain Hoechst 33342 and analyzed by live cell confocal imaging. Images are representative of three independent experiments. Scale bar represents 10 μm.

Sodium butyrate does not result in increased levels of Reactive Oxygen Species (ROS) in neuronal-like PC12-ND6 cells. On the basis that increased $\Delta\Psi_m$ could result in elevated ROS levels due to electron leakage through the mitochondrial electron transfer chain (ETC), the relative levels of superoxide anions ($O_2^-$) were measured by live cell confocal microscopy using the redox-sensitive fluorogenic live-cell permeant dye MitoSOX™, as described in Uittenbogaard et al., 2010b. NaBt exposure failed to generate ROS production (FIG. 10).

Figures 11A, 11B, 11C, 11D:
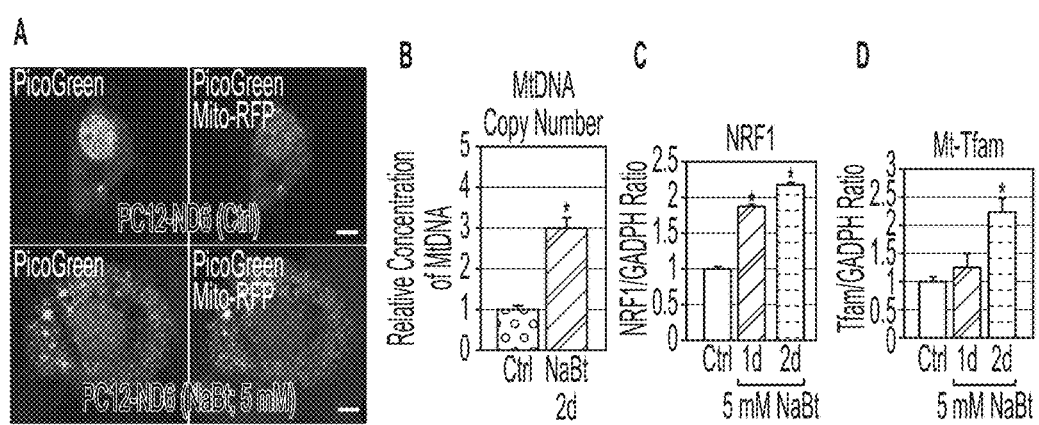
FIG. 11A-11D are images from microscopy and graphs showing NaBt promotes mtDNA replication via the NRF-1/Tfam axis. (A) Confocal analysis of mtDNA foci; scale bar=5 (B) Quantitative analysis of mtDNA copy number by PCR; *p<0.001. (C, D) Quantitative immunoblot analysis of NRF-1 and Tfam; *p<0.001.

NaBt enhances mtDNA replication via the PGC1α-mediated NRF-1/Tfam axis. It was investigated whether NaBt enhanced mtDNA replication using the PicoGreen® dye to label mtDNA. PC12-ND6 cells were transfected with the mito-dsRed vector prior to NaBt treatment followed by PicoGreen® staining. Live cell confocal microscopy revealed an increased number of mtDNA foci in treated cells (FIG. 11A), which was confirmed by quantitative PCR (FIG. 11B). To corroborate enhanced mitochondrial biogenesis, two key target genes of PGC1α were examined, the NRF-1 transcription factor and its direct target gene Tfam, both essential for mitochondrial biogenesis. NRF-1 expression increased on day 1 of NaBt treatment followed by induced Tfam expression on day 2 (FIG. 11C, D). Gene expression levels of these two key markers of mitochondrial biogenesis at one and two days of treatment were measured, as their expression triggers biogenesis of mitochondria, which is optimal after three days of NaBt exposure (FIG. 6). The findings confirm the NaBt-mediated modulation of mitochondrial biogenesis and mtDNA replication in neuronal cells.

Figures 12A, 12B:
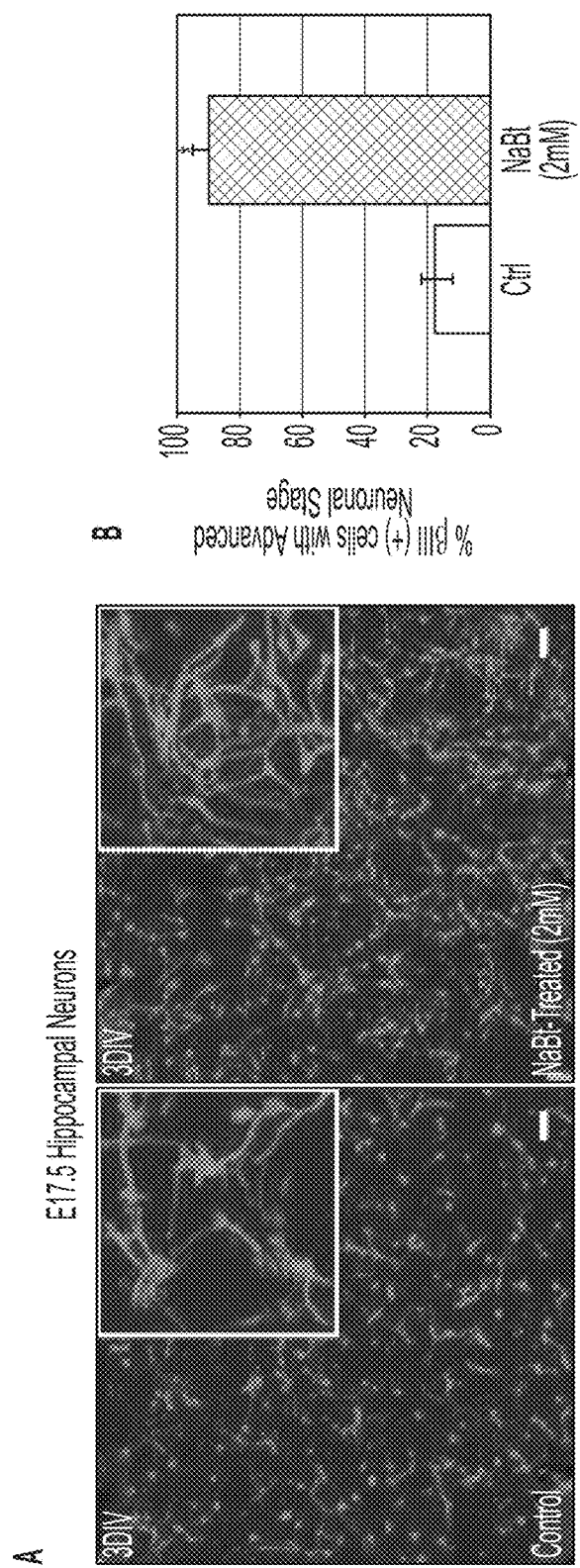
FIG. 12A-12B are images from microscopy and a graph showing that NaBt concomitantly increases the mitochondrial biomass of E17.5 hippocampal progenitor cells and their neuronal differentiation. (A) High-resolution tile-stacked confocal micrographs of untreated and NaBt-treated E17.5 hippocampal neurons labeled with β-III tubulin (red) and nuclear counterstain DAPI (blue) at 3DIV with insets showing high magnification of the neuritic network. Scale bar represents 20 μm. (B) Graph of percent of β-III tubulin$^+$ cells having reached the neuronal stage 3. Mean±S.D. (n=250 cells for each condition; *p=0.0001).

Sodium butyrate-mediated increase in mitochondrial mass correlates with accelerated and enhanced neuronal differentiation of hippocampal progenitor cells. Since broad spectrum HDACis induce neuronal differentiation of adult neural progenitors (reviewed by Lee and Lee, 2010), it was assessed whether increase in mitochondrial mass upon NaBt exposure could accelerate the timing of the neuronal developmental stages of cultured E17.5 hippocampal progenitor cells in the absence of astroglial trophic support. To test this hypothesis, the well-defined chronology of the distinct phenotypic differentiation stages of cultured embryonic hippocampal cells was relied on. While cells undergo rapid but asynchronous transition from stage 1 to stage 2, cells generally remain in stage 2 for up to 36 hours before initiating developmental stage 3, making this asynchronous transition slow and spanning over three to four days of culture, a temporal sequence that was determined in the presence of a glial monolayer (Kaech and Banker, 2006). Dissociated E17.5 hippocampal cells were plated in the absence of glial feeder layer and untreated or treated with NaBt (2 mM) at 1DIV (Day In Vitro). At 3DIV, cells were immunostained for the pan-neuronal marker β-III tubulin to quantify the percent of cells at stage 3. Exposure to NaBt resulted in a markedly accelerated neuronal differentiation, as evidenced by 90% of treated E17.5 hippocampal neurons having advanced to stage 3 and exhibiting a dense neuritic network, while only 20% of untreated E17.5 neurons reached developmental stage 3 forming a loose neuritic network (FIG. 12). Given the fact that NaBt increased the mitochondrial volume in treated E17.5 hippocampal neurons (FIG. 7A), the collective results indicate a correlation between mitochondrial mass and neuronal differentiation of hippocampal progenitor cells, suggestive of mitochondrial biogenesis being an integral component of the neuronal differentiation process.

Figures 13A, 13B, 13C, 13D, 13E:
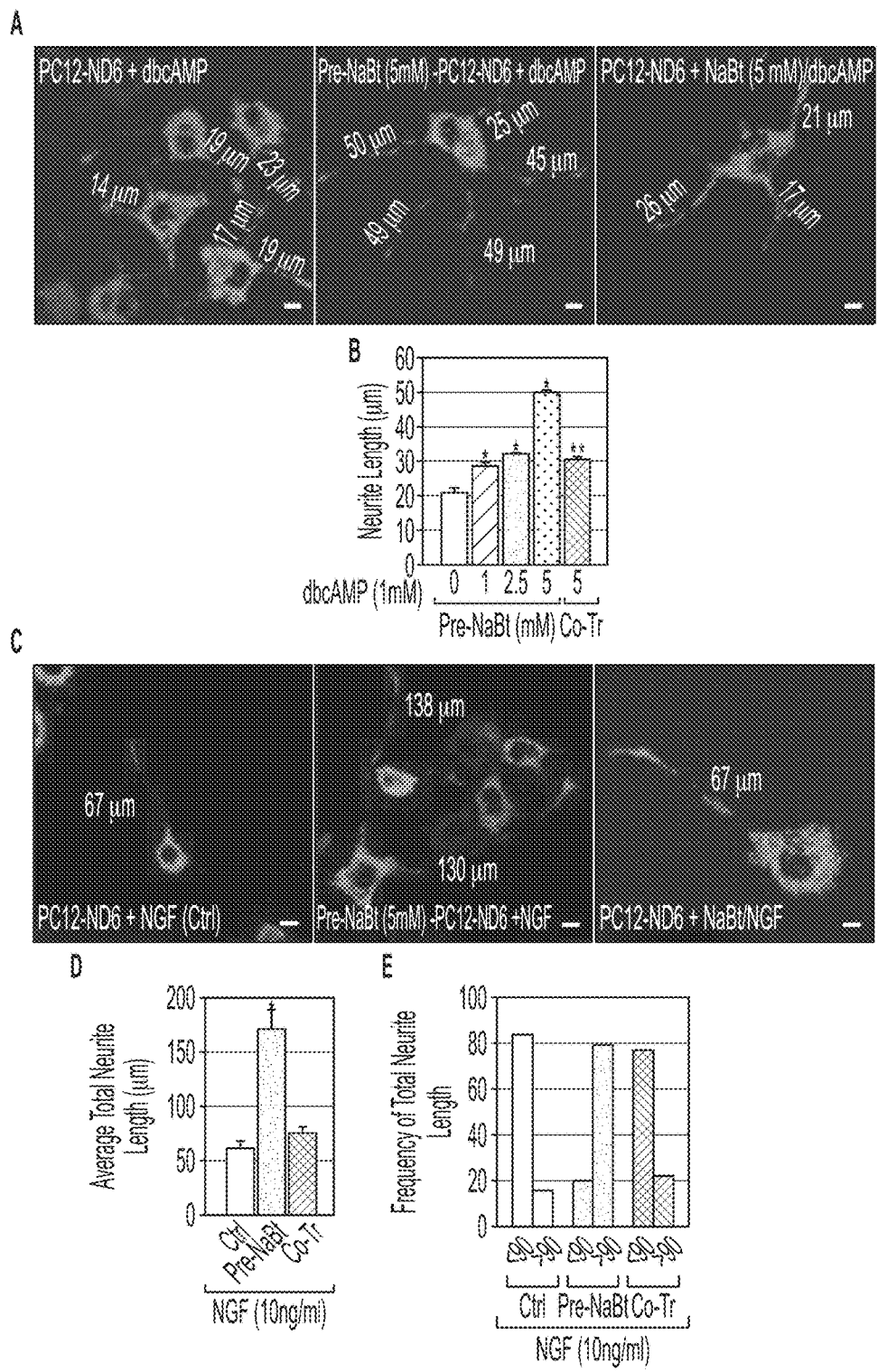
FIG. 13A-13E are images from microscopy and graphs showing that the timing of NaBt treatment is critical for enhancing neuronal differentiation of PC12-ND6 cells upon sub-optimal neurotrophic cues. (A) Confocal micrographs of PC12-ND6 cells treated with dbcAMP alone or with NaBt (5 mM) in a simultaneous or sequential manner. Scale bar represents 5 μm. (B) Graph of neurite length. Mean±SEM (n=50 for each condition; compared to control (no NaBt) *p=0.0001 and **p=0.0009). (C) Confocal micrographs of PC12-ND6 cells treated with sub-optimal NGF concentration (10 ng/ml) alone or first NaBt (5 mM) in a simultaneous or sequential manner. Scale bar represents 10 μm. (D) Graph of average total neurite length. Mean±SEM (n=50 for each condition; compared to control *p=0.0001). (E) Graph of the frequency of total neurite length below and above 90 μm.

The timing of NaBt pre-treatment is critical for enhancing neuronal differentiation of PC12-ND6 cells and potentiating sub-optimal neurotrophic cues. We next investigated whether NaBt-mediated increase of mitochondrial biogenesis could potentiate subsequent sub-optimal neurotrophic cues to trigger effective neurite outgrowth in PC12-ND6 cells and whether a temporal window for NaBt responsiveness might exist. We took advantage of the well-established experimental paradigm, dbcAMP, which can only elicit neurite initiation characterized with limited length (15-20 μm) in the PC12 cell system (Gunning et al., 1981; Uittenbogaard and Chiaramello, 2004). PC12-ND6 cells were transfected with the vector mito-GFP and then treated with different concentrations of NaBt for three days prior to dbcAMP (1 mM) exposure for 24 hours. Pre-treatment with NaBt potentiated the neuritogenic activity of dbcAMP in a dose-dependent manner, with neurite length reaching 50 μm at the highest dose of NaBt (FIGS. 13A and B). In contrast, co-addition of NaBt (5 mM) and dbcAMP (1 mM) severely dampened the NaBt effect on increased neuritogenesis observed upon sequential treatment of PC12-ND6 cells (FIGS. 13A and B), suggestive of a critical time window during which acquisition of adequate mitochondrial mass occurs during the early stages of neuritogenesis.

NaBt-mediated modulation of the neuronal potential of PC12-ND6 cells in the context of sub-optimal NGF concentration (10 ng/ml) was further investigated. Transfected PC12-ND6 cells were first treated with NaBt (5 mM) for three days prior to NGF exposure (10 ng/ml). A time course analysis of neurite outgrowth was conducted during the first two days of NGF exposure by live-cell confocal microscopy. NaBt pre-treatment of PC12-ND6 cells resulted in accelerated neuritogenesis after 24 hours of NGF exposure, with an average total neurite length of 168 μm, whereas control PC12-ND6 cells showed a lesser neurite extension characterized with an average total length of only 60 μm (FIGS. 13C and D). Furthermore, pre-treatment with NaBt altered the frequency of neurite length with pre-treated PC12-ND6 cells exhibiting 79% of their neurites longer than 90 μm, while only 16% of control NGF-treated PC12-ND6 cells displayed similar neurite length (FIG. 13E). Such trend of neurite extension was maintained at day 2 of NGF exposure with NaBt-pre-treated or co-treated PC12-ND6 cells. Whether NaBt added concomitantly with NGF (10 ng/ml) could mediate increased neuritogenesis was also assessed. No synergistic effect between NaBt and NGF on neurite outgrowth was observed when administered simultaneously, in keeping with the curtailed effect of NaBt while co-administered with dbcAMP (FIG. 13B). Collectively, these results suggest that NaBt-mediated mitochondrial biogenesis may need to precede terminal neuronal differentiation.

Mitochondrial biogenesis is a pre-requisite step for neuronal differentiation. To test the hypothesis that mitochondrial biogenesis is an essential step during the early stages of neuronal differentiation chloramphenicol was used to modulate the mitochondrial biomass of PC12-ND6 cells and E17.5 hippocampal neurons. Low doses of chloramphenicol selectively inhibit mitochondrial translation without interfering with translation of nuclear-encoded proteins and consequently block mitochondrial biogenesis (Balbi, 2004).

Figures 14A, 14B, 14C, 14D, 14E:
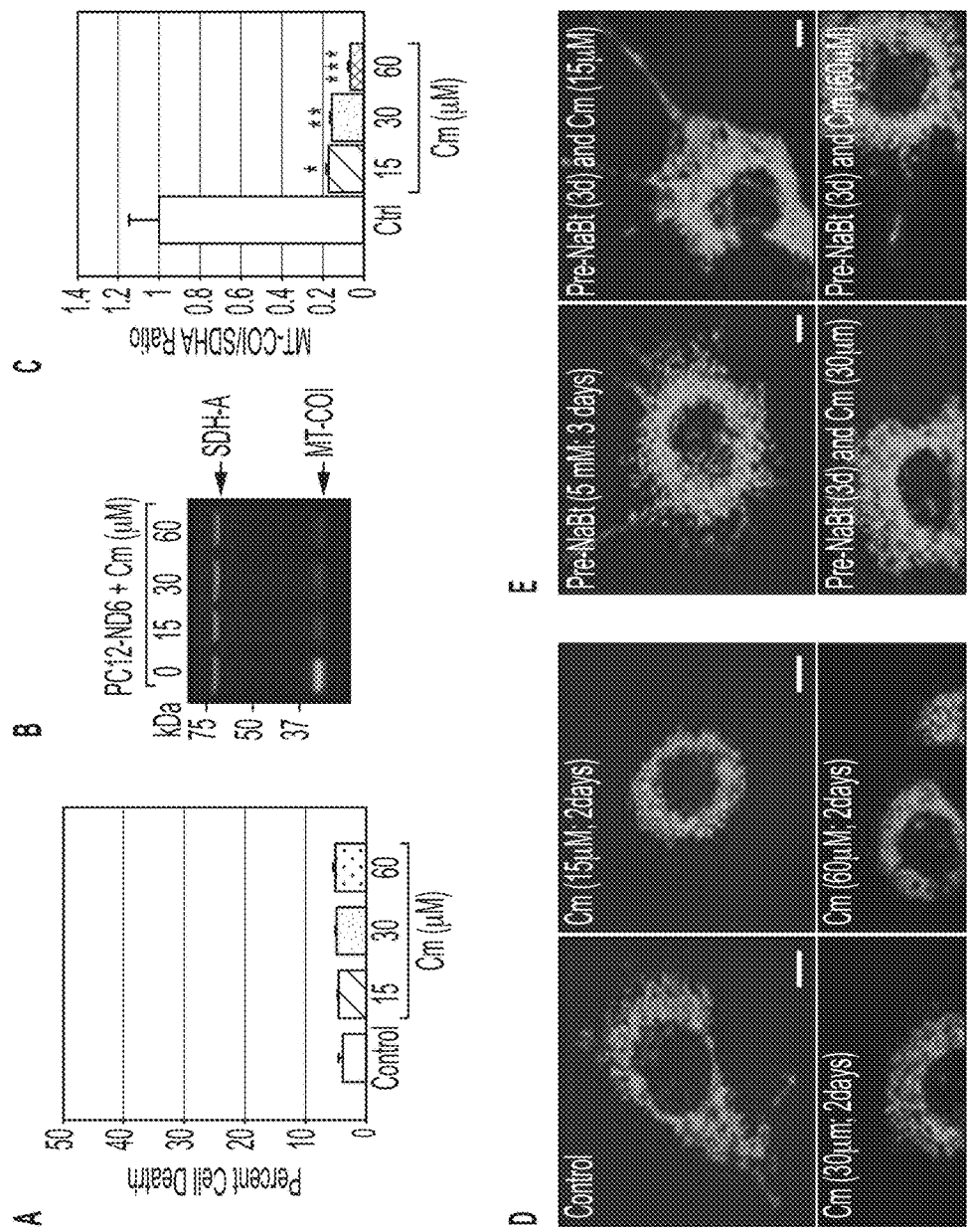
FIG. 14A-14E are images from microscopy showing that pre-treatment of PC12-ND6 cells with NaBt prevents chloramphenicol-mediated decrease of mitochondrial mass. (A) Graph of PC12-ND6 cell death upon exposure to different concentrations of chloramphenicol (Cm). Percent of cell death±SEM (n=250 cells). (B) Quantitative immunoblot analysis of mitochondrial-encoded MT-CO1 protein (green) and nuclear-encoded SDH-A protein (red) in Cm-treated PC12-ND6 cells. (C) Graph of MT-CO1/SDH-A ratio normalized to untreated PC12-ND6 cells. Mean±SEM (n=3; compared to untreated cells *p=0.0052, p=0.0048, and *p=0.0034). (D) Confocal micrographs of untreated and Cm-treated PC12-ND6 cells transfected with the vector mito-GFP. Scale bar represents 5 μm. (E) Confocal micrographs of NaBt pre-treated PC12-ND6 cells transfected with the vector mito-GFP and exposed to Cm. Scale bar represents 5 μm.

PC12-ND6 cell viability in the presence of increasing concentrations of chloramphenicol (0, 15, 30, and 60 μM) for two days by live-cell confocal microscopy and found negligible cell death associated with these concentrations (FIG. 14A) was assessed. The efficacy of chloramphenicol treatment was determined by simultaneously examining the expression levels of the nuclear-encoded succinate dehydrogenase (SDH-A) subunit of Complex II and the mitochondrial-encoded subunit I of Complex IV (MT-COI) using a quantitative immunoblot approach. While none of the chloramphenicol concentrations altered the SDH-A expression levels, the lowest dose of chloramphenicol abolished most of MT-COI expression (FIG. 14B). The effect of chloramphenicol on mitochondrial mass by live-cell confocal microscopy using PC12-ND6 cells transfected with the vector mito-GFP was confirmed. Chloramphenicol-treated PC12-ND6 cells displayed a concentration-dependent decrease of mitochondrial mass, while pre-treatment with NaBt prior to chloramphenicol exposure enabled PC12-ND6 cells to sustain their mitochondrial biomass even at the highest concentration of chloramphenicol (FIG. 14C).

Figures 15A, 15B, 15C:
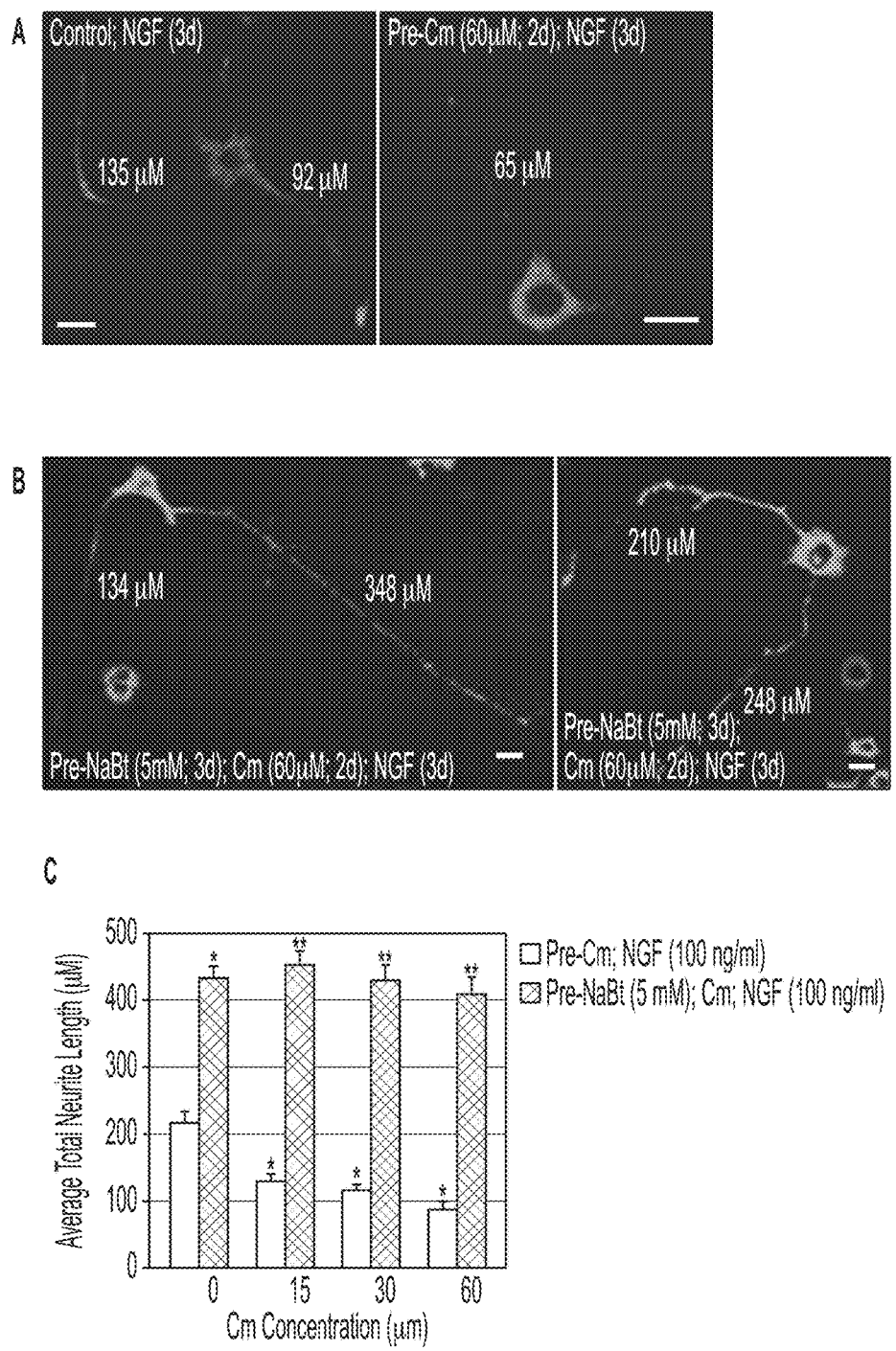
FIG. 15A-15C are images from microscopy and a graph showing that Pre-treatment of PC12-ND6 cells negates the inhibitory effect of chloramphenicol on NGF-mediated neuronal differentiation. (A) Confocal micrographs of untreated and Cm-treated PC12-ND6 cells transfected with the vector mito-GFP and exposed to NGF. Scale bar represents 20 μm. (B) Confocal micrographs of NaBt pre-treated PC12-ND6 cells transfected with the vector mito-GFP and exposed to chloramphenicol prior to NGF treatment. Scale bar represents 20 μm. (C) Graph of average total neurite length. Mean±SEM (n=50 cells; compared to untreated PC12-ND6 cells *p=0.0001; compared to non-NaBt-treated PC12-ND6 cells with corresponding Cm concentration **p=0.0001).

To test the hypothesis that acquisition of a critical pool of mitochondria prior to the onset of neuronal differentiation is a rate-limiting step for executing differentiation, PC12-ND6 cells were treated with increasing doses of chloramphenicol for two days prior to NGF exposure (100 ng/ml) and monitored total neurite length after three days of NGF treatment. It was found that chloramphenicol compromised NGF-mediated neurite outgrowth by causing a 43% reduction in total neurite length at the lowest concentration (FIGS. 15A and C). Based on the results that NaBt endows PC12-ND6 cells with increased mitochondrial mass through biogenesis, resulting in accelerated neuronal differentiation, it was examined whether exposure to NaBt for three days could confer protection to chloramphenicol-mediated inhibition of neuronal differentiation upon NGF signaling. It was found that NaBt-treated PC12-ND6 cells maintained a robust neuritogenesis triggered by NGF signaling, as their total neurite length remained unaffected even in the presence of the highest concentration of chloramphenicol (FIGS. 15B and C). Furthermore, NaBt-pre-treated PC12-ND6 cells prior to exposure to 60 μM of chloramphenicol still retained a high mitochondrial density in their processes, which stands in contrast with control chloramphenicol-treated PC12-ND6 cells (FIGS. 15A and B). Collectively, these results suggest that modulation of the mitochondrial pool prior to neurotrophic cues dictates the efficiency of initiation of neuronal differentiation during the transition from progenitor to differentiating neuronal cells, suggestive of mitochondrial biogenesis being a rate-limiting step of that process.

Figures 16A, 16B, 16C, 16D, 16E, 16F, 16G, 16H, 16I:
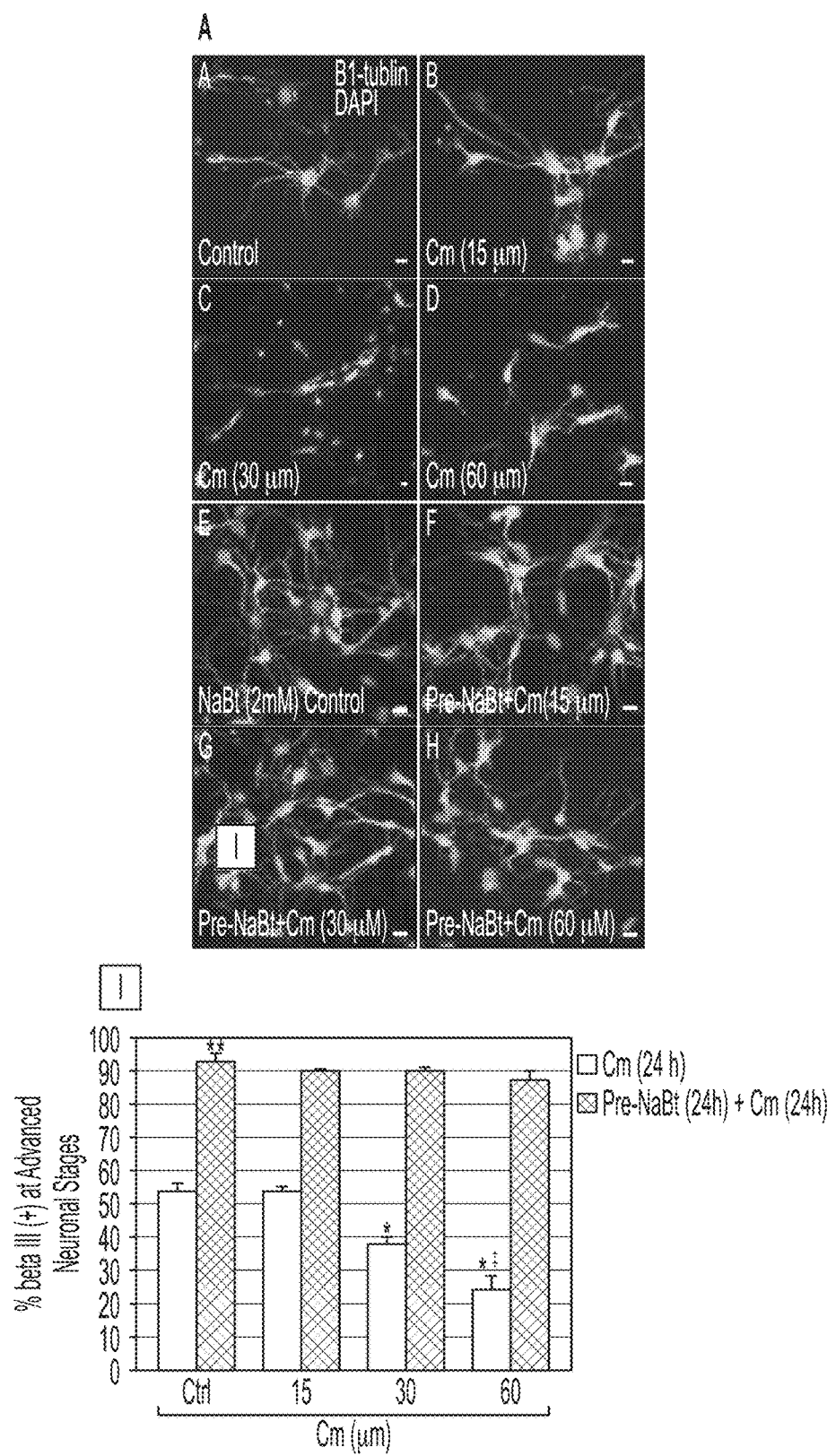
FIG. 16A-16I are images from microscopy and a graph showing that Pre-treatment of E17.5 hippocampal neurons with NaBt protects against chloramphenicol-induced loss of neuronal differentiation. (A-D) Confocal micrographs of E17.5 hippocampal neurons exposed to different concentrations of chloramphenicol at 2DIV and labeled with anti tubulin antibody (red) and nuclear counterstain DAPI (blue) at 3DIV. Scale bar represents 10 μm. (E-H) Confocal micrographs of E17.5 hippocampal neurons treated with NaBt (2 mM) at 1DIV prior to exposure to different concentrations of chloramphenicol at 2DIV and labeled with anti tubulin antibody (red) and nuclear counterstain DAPI (blue) at 3DIV. Scale bar represents 10 μm. (I) Graph of E17.5 β-III+ hippocampal neurons at the neuronal stage 3. Mean±S.D. (n=250 cells; compared to untreated control *p=0.0001; compared to the corresponding non-NaBt treated sample **p=0.0001; compared to non-NaBt treated cells exposed to Cm at 30 μM‡p=0.007).

The consequences of chloramphenicol exposure on untreated or NaBt-treated E17.5 hippocampal neurons was examined. At 1DIV, dissociated E17.5 hippocampal neurons were switched to differentiation medium in the absence or presence of NaBt (2 mM) for 24 hours before being treated with increasing concentrations of chloramphenicol (0, 15, 30, and 60 μM) for 24 hours. At 3DIV, their phenotypic differentiation was examined by immunocytochemistry using an antibody against the pan-neuronal marker β-III tubulin and quantified the percent of neurons having reached the developmental stage 3 for each experimental condition. As expected, only half of untreated neurons reached stage 3 in the absence of NaBt, while more than 90% of NaBt-treated neurons achieved such degree of differentiation, thereby forming an elaborate neuritic network (FIGS. 16A, E, and I). Chloramphenicol treatment of E17.5 hippocampal neurons in the absence of NaBt pre-treatment caused a decreased frequency of neuronal stage 3, a response that was concentration-dependent (FIG. 16B-D). Only the lowest concentration of chloramphenicol (15 μM) did not alter the percent of neurons at stage 3, while higher concentrations (30 and 60 μM) resulted in a 27% and 54% decreased transition to stage 3, respectively (FIG. 16I). In contrast, treatment of E17.5 hippocampal neurons with NaBt prior to chloramphenicol exposure sustained the frequency of advanced neuronal stage, even at high concentration of chloramphenicol (60 μM) (FIG. 16E-6I). Thus, these results are congruent with the notion that acquisition of a critical mitochondrial biomass precedes execution of terminal differentiation, a step that is essential for efficient transition from progenitors to differentiated neurons and under epigenetic regulation.

Figures 17A, 17B, 17C:
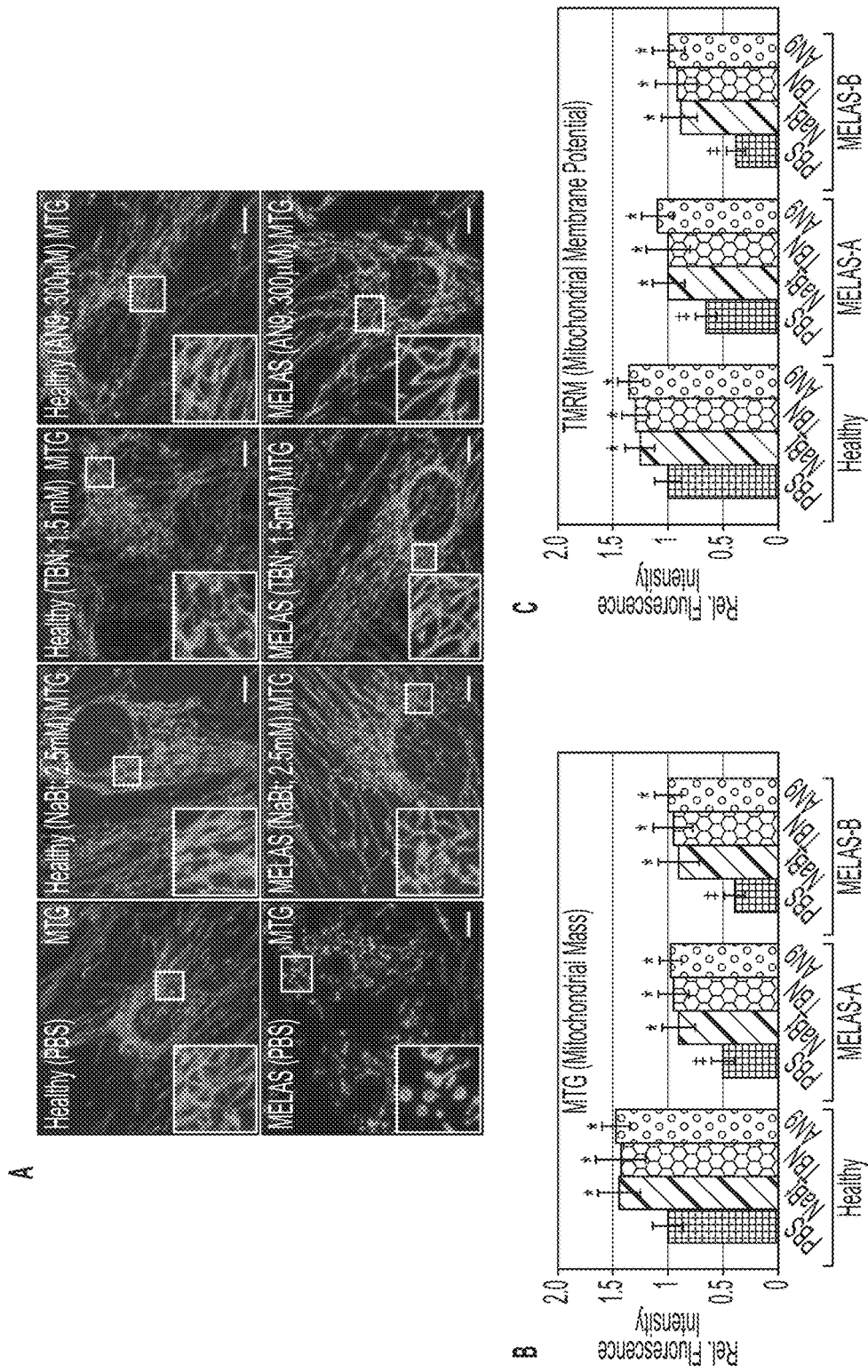
FIG. 17A-17C are images from microscopy and graphs showing that butyrates rescue the mitochondrial phenotype in MELAS fibroblasts. (A) Confocal analysis of healthy and MELAS fibroblasts treated as indicated and labeled with the MTG dye; scale bar=10 (B) Analysis of the mitochondrial mass; n=3 (60 cells per experiment; ‡p<0.05, unpaired T-test *p<0.05, paired T-test). (C) Analysis of $\Delta_{\psi m}$ (‡p<0.05, unpaired T-test; *p<0.05, paired T-test).

Butyrates rescue the mitochondrial mass, morphology, networking, membrane potential, and cellular ATP levels in MELAS fibroblasts. Skin fibroblasts from two MELAS patients and from a healthy subject as a control were used. Dose-dependent analyses of butyrates to determine their best concentrations for eliciting an optimal mitochondrial response without cellular toxicity was performed. Healthy and MELAS fibroblasts were treated with PBS, NaBt (2.5 mM), TBN (1.5 mM), or AN9 (300 µM) for three days before labeling with the MTG dye for live cell confocal analysis. PBS-treated MELAS fibroblasts exhibited reduced mitochondrial mass, mitochondria with fragmented and swollen morphology, as well as abnormal mitochondrial networking, compared to PBS-treated healthy fibroblasts (FIG. 17A). A three-day exposure to NaBt, TBN, or AN9 restored normal mitochondrial mass, morphology, and networking in MELAS fibroblasts (FIG. 17A, B). Using the TMRM dye, it was found that PBS-treated MELAS fibroblasts displayed a lower mitochondrial membrane potential ($\Delta_{\psi m}$) compared to PBS-treated healthy fibroblasts (FIG. 17C). Thus, MELAS fibroblasts were treated with the butyrates before TMRM labeling and found that they restored normal levels of $\Delta_{\psi m}$; this confirms restoration of the mitochondrial network, a $\Delta_{\psi m}$-dependent process (FIG. 17C).

Figure 18:
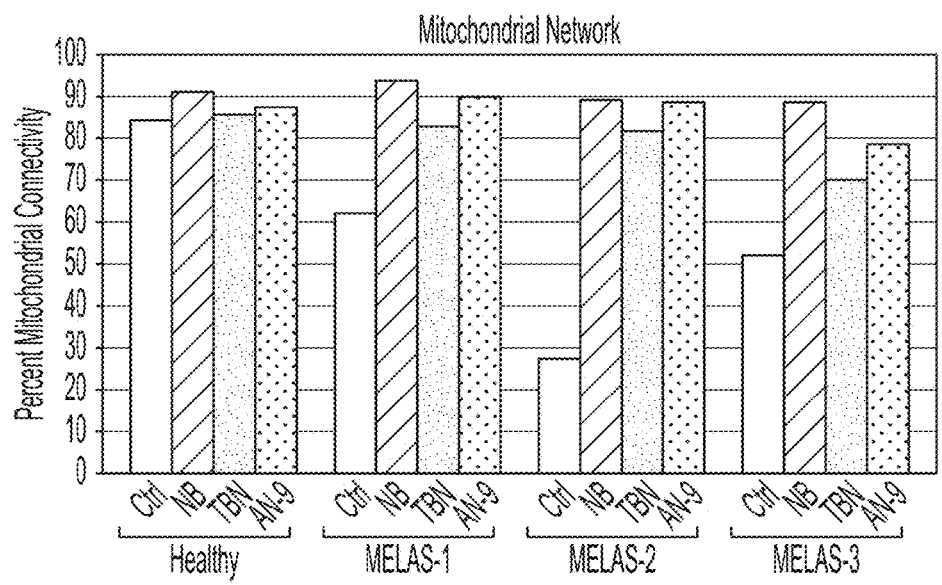
FIG. 18 is a graph showing that butyrate and its derivatives rescue the mitochondrial dynamics and connectivity in MELAS fibroblasts. Confocal analysis of MTG-labeled healthy and MELAS fibroblasts from three patients was carried out using Image J and revealed that NaBt and its derivatives, TBN and AN-9, rescue the connectivity among mitochondria (n=3; 60 cells per experiment were counted).
Figure 19:
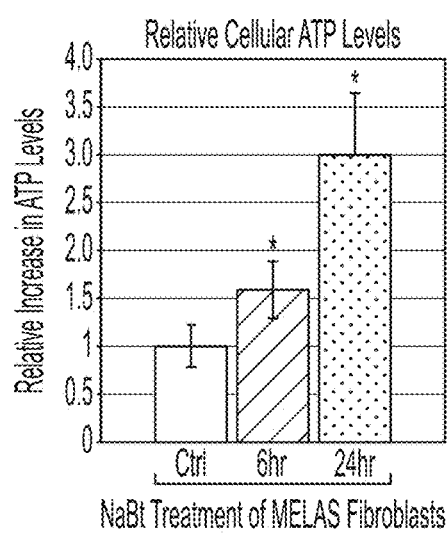
FIG. 19 is a graph showing that NaBt augments the relative cellular ATP levels in MELAS fibroblasts. The relative cellular ATP content was examined by a fluorescent probe, magnesium green (Mg Gr). MELAS fibroblasts were treated for 6 and 24 hours with NaBt (2.5 m M) before being labeled with Mg-Gr. Confocal analysis of Mg Green-labeled MELAS fibroblasts revealed an increase in relative cellular ATP levels after six hours of NaBt exposure, which became more accentuated after 24 hours of treatment (n=3; *p<0.05; unpaired T-test).

Morphometric analysis using Image J revealed that butyrates increased the percent of connected and elongated mitochondria similar to that of PBS-treated healthy fibroblasts (FIG. 18). The duration of this rescue was probed by withdrawing butyrates from the medium and found that the rescued mitochondrial phenotype was kept up to ten days.

Finally, it was investigated whether NaBt could improve the ATP cellular levels in MELAS fibroblasts, as suggested by the amelioration of mitochondrial biomass and its connectivity. To assess relative cellular ATP levels in live MELAS fibroblasts, the fluorescent magnesium green (Mg-Gr) dye, which has been successfully employed in live patient fibroblasts, was used. Fluorescence emission from the Mg-Gr dye is directly proportional to the concentration of intracellular free Mg2+ concentration. Since the affinity of Mg2+ for ATP is about ten times higher than its affinity for ADP or AMP, the fluorescence intensity is inversely correlated with the intracellular levels of ATP. A time course exposure to NaBt (5 mM) was performed using MELAS fibroblasts from one patient that has been comprehensively evaluated in terms of mitochondrial mass, mitochondrial membrane potential, and mitochondrial dynamics and networking (FIGS. 17 and 18). By live-cell confocal microscopy, a steady increase in relative cellular ATP levels during the first 24 hours of NaBt (2.5 mM) treatment was observed. These results are congruent with increased bioenergetic capacity of mitochondria, as measured with the TMRM dye for assessing the mitochondrial membrane potential (FIG. 17C). Thus, butyrates augment the functional mitochondrial mass in dermal MELAS fibroblasts, thereby reversing their deficits in mitochondrial mass and bioenergetics capacity.

In conclusion, the collective results provide the first evidence of the promising therapeutic potential of NaBt and its derivatives, as pharmacological agents able to mitigate the mitochondrial deficit characteristic of MELAS. The results show that mitochondria respond favorably to butyrate-mediated chromatin reprogramming via specific histone acetylation, while synergizing key mitochondrial-nuclear crosstalk by generating mitochondrial acetyl-CoA and ATP, both vital for epigenetic modulation of nuclear gene expression and mitochondrial physiology.

Example 2

Project Summary/Abstract

The most common mitochondrial respiratory disorder is MELAS (Mitochondrial Encephalopathy Lactic Acidosis with Stroke-like Episodes), an incurable progressive neurodegenerative disease with early childhood onset. This orphan disease causes heterogeneous clinical symptoms, such as encephalopathy, seizures, stroke-like episodes, cognitive impairment, chronic lactic acidosis, and myopathy. Most MELAS patients harbor a maternally inherited mutation (A3243G) in the mitochondrial-encoded tRNA$^{Leu/UUR}$ gene, which affects the oxidative phosphorylation (OXPHOS) system responsible for ATP synthesis. In MELAS cells, the multi-copy mitochondrial genome population is heterogeneous, with variable ratios of mutant mtDNAs and wild type (WT) mtDNAs, a state known as heteroplasmy. Individuals with the MELAS mutation become symptomatic only when the mutant load exceeds a certain threshold of heteroplasmy. Currently, no therapeutic options are available to prevent the progression of the disease, resulting in significant disability, a poor prognosis, and premature death.

An embodiment of the novel pharmacological approach described herein uses butyrates to promote nuclear and mitochondrial metabolic reprogramming by boosting mitochondrial biogenesis and maximizing residual ATP output. Using primary fibroblasts derived from a skin biopsy of two MELAS patients, an Affymetrix-based genome-wide microarray analysis that revealed enrichment of pathways for mitochondrial biogenesis and bioenergetics upon exposure to butyrates was performed. From live cell confocal microscopy, it was found that butyrates restored the mitochondrial mass and the pool of bioenergetically competent mitochondria in MELAS fibroblasts. In healthy neuronal cells, it was found that butyrates induced mitochondrial biogenesis via expression of essential nuclear-encoded regulators and augmented the pool of bioenergetic mitochondria and ATP levels. Thus, the data validate a pharmaco-epigenomic approach and establish proof-of-principle. It was hypothesized that butyrates can augment the functional mitochondrial mass in skin fibroblasts from 20 MELAS patients. Fibroblasts from this number of patients, each with different nuclear backgrounds and heteroplasmic loads, will ensure the findings extend beyond a case study into a statistically sound and broadly applicable report. It will be tested whether butyrates: (Aim 1) induce favorable mitochondrial biogenesis, thereby shifting heteroplasmy toward healthy mitochondria; and (Aim 2) maximize ATP output via optimization of OXPHOS activity and a metabolic shift toward fatty acid beta oxidation. It is anticipated to identify the most promising butyrate candidate for alleviating the symptoms of the MELAS disease. The proposed study will set the stage for future clinical studies with the Children's National Medical Center and the North American Mitochondrial Disease Consortium, in concordance with the PAR-13-023 issued by the NINDS Office of Translational Research for R21 exploratory projects.

Introduction

With regard to the notion that "wild type (WT) and mutant mitochondrial DNA inside heteroplasmic cells is segregated into "healthy" and "unhealthy" mitochondria", complexities of heteroplasmy are explained. In brief, heteroplasmy occurs at: 1) the organellar level (intra-mitochondrial heteroplasmy), when both WT and mutant mtDNAs are present within a mitochondrion (FIG. 2A); and 2) the cellular level (inter-mitochondrial heteroplasmy), when both healthy and diseased mitochondria are present within a cell (FIG. 2B). A mitochondrion is considered healthy if its WT mtDNAs maintain a certain threshold, keeping its mutant mtDNAs in check; a mitochondrion is diseased if its mutant mtDNAs surpass that threshold, overwhelming its WT mtDNAs. Heteroplasmy is dictated by the ratio of both WT and mutant mtDNAs—this does not suggest that healthy mitochondria harbor only WT mtDNAs and diseased mitochondria only mutant mtDNAs.

In healthy individuals, constant cycles of fusion and fission among mitochondria maintain a homogenous mitochondrial population and a low frequency of mutant mtDNAs. Fusion, which requires a high mitochondrial membrane potential, allows the exchange of mitochondrial content, including mtDNAs, which dampens the deleterious effects of mtDNA mutations. Also, mitochondria with low membrane potential cannot undergo fusion and are degraded by mitophagy, thus preserving the population of functional mitochondria in healthy cells. In contrast, MELAS patients harbor a preponderance of mutant mtDNAs, which worsens over time, resulting in enrichment of diseased mitochondria. Our preliminary results with fibroblasts from two MELAS patients show a heterogeneous mitochondrial population of some healthy and numerous diseased mitochondria with a fragmented morphology, indicative of compromised fusion (FIG. 23). Furthermore, MELAS fibroblasts had an overall substantially lower mitochondrial membrane potential, which prevents fusion and therefore an even distribution of mutant mtDNAs among mitochondria. In MELAS cells, inter-mitochondrial heteroplasmy is further compounded by defective clearance of dysfunctional mitochondria.

The data described herein provide DIRECT evidence that butyrates increase mitochondrial density and the pool of bioenergetic mitochondria, while restoring their normal dynamics (FIG. 23). A dose-dependent study is performed, as in the preliminary study with two MELAS patients. In collaboration with a biostatistician, the statistical plan has been revamped and power calculation validating our number of MELAS patients. Microarray analysis confirms that NaBt showed limited off-target effects in MELAS fibroblasts.

In regard to the idea that MELAS would resolve itself over time due to constant mitochondrial turnover—in addition to defective mitochondrial turnover via mitophagy, MELAS cells carry a small pool of healthy mitochondria to begin with, which is not sufficient to trigger a physiologically relevant heteroplasmic shift in favor of functional mitochondria. The strategy aims to pharmacologically boost this endogenous mitobiogenic response. In that boosting mitochondrial biogenesis may worsen stroke-like episodes in MELAS patients—this maladaptive response is addressed in endothelial and smooth muscle cells of small arteries that almost exclusively favors proliferation of diseased mitochondria. The data on MELAS fibroblasts suggest that butyrates may ease the burden of diseased mitochondria in small arteries and therefore also stroke-like episodes. Mitochondrial biogenesis is measured using five molecular approaches: two MitoTracker® dyes, the mito-GFP or mito-dsRed vector, the PicoGreen® dye, antibodies against mtDNA, COXα and SOD2, and quantitative PCR (FIGS. 4-6). In addition, ATP levels and ATP/AMP ratio are assessed using luciferase-based assays combined with Seahorse-based assays and technology.

Proteomic studies will be pursued in the project.

Regarding "The Aims call for very high drug concentrations (0.1 to 5 mM)", the dose-dependent preliminary study on MELAS fibroblasts determined the optimal concentrations of NaBt (2.5 mM), TBN (1.5 mM), and AN9 (300 μM) for eliciting maximal mitochondrial biogenesis without cellular toxicity (FIG. 23). These concentrations are in accordance with their known half-maximal activity ($IC_{50}$). TBN and AN9 at these concentrations can be administered orally without toxicity or side effects in patients. TBN replaces the drug phenylbutyrate.

Research Design (a) Significance: MELAS (Mitochondrial Encephalopathy with Lactic Acidosis and Stroke-like episodes) is a fatal mitochondrial respiratory disorder (MRD) [1-4]. This progressive neurodegenerative disease has an early onset of heterogeneous clinical symptoms that include encephalopathy, seizures and stroke-like episodes, dementia, ataxia, migraine-like headaches, cognitive impairment, chronic lactic acidosis, cyclical vomiting, hypertrophic cardiomyopathy, myopathy, deafness, and diabetes [5-12]. Currently, no therapeutic options are available to these patients, resulting in significant disability, a poor prognosis, and premature death [8-10]. The devastation wrought by MELAS underscores the urgent need to develop therapeutic strategies.

MELAS is defined by insufficient ATP levels, caused by a mutation in the mitochondrial genome that affects the oxidative phosphorylation (OXPHOS) system. ATP is produced upon electron transfer through the first four OXPHOS complexes, with complexes I and II being the two points of entry for electrons and ATP synthesis occurring at complex V (FIG. 1). In MELAS, complex I is deficient, leading to insufficient ATP production. The proposed novel pharmacological approach uses butyrates to promote nuclear and mitochondrial metabolic reprogramming for mitigating the chronic energy deficit in MELAS (FIG. 1). Nuclear reprogramming increases mitochondrial biogenesis and therefore ATP levels, while mitochondrial metabolic reprogramming bypasses the defective complex I and enhances the activity of downstream complexes to boost ATP production (FIG. 1).

The MELAS mutation only affects a subset of the multicopy mitochondrial genome, causing heteroplasmy. Most MELAS patients exhibit a maternally-inherited A to G substitution at position 3243 of the mitochondrial gene for $tRNA^{Leu(UUR)}$, known as the A3243G MELAS mutation, which mainly affects complex I due to its high leucine content [13, 14]. Although the prevalence of this disease is rare (1 in 15,000), the MELAS mutation has been detected in newborn cord bloods at the much higher frequency of 1 in 750 [15-19]. This difference stems from the variable ratios of mutant mtDNAs and wild type (WT) mtDNAs co-existing within cells, a state known as heteroplasmy [25-22]. Individuals with the MELAS mutation become symptomatic only when the mutant load of diseased mitochondria exceeds a certain threshold (FIG. 2B).

MELAS patients display heteroplasmy at the organellar level (intra-mitochondrial heteroplasmy) and the cellular level (inter-mitochondrial heteroplasmy) [2, 16, 23-30]. Intra-mitochondrial heteroplasmy stems from the presence of both WT and mutant mtDNAs within a mitochondrion; this results in inter-mitochondrial heteroplasmy, a mixed population of healthy (functional) and diseased (dysfunctional) mitochondria (FIGS. 2A and 2B) [31-35]. A mitochondrion is considered diseased/dysfunctional if its mutant mtDNAs surpass a certain threshold, overwhelming its WT mtDNAs, and vice versa for healthy/functional mitochondria (FIG. 2A). Although the mechanism that progressively enriches the MELAS mutation remains largely unknown, emerging evidence suggests defective mitochondrial dynamics and turnover. In healthy cells, dynamic fusion-fission events lead to effective inter-mitochondrial exchange; this exchange "normalizes" the distribution of mutant mtDNAs among mitochondria with high mitochondrial membrane potential [36-40]. In MELAS cells, diseased mitochondria are severely depolarized, which compromises inter-mitochondrial exchange via fusion [41], resulting in heteroplasmy (FIG. 2B). Moreover, ineffective clearance of diseased mitochondria via mitophagy further aggravates heteroplasmy over time in somatic cells [42-44]. Our recent data show that MELAS fibroblasts have a disrupted mitochondrial network with abundant fragmented and depolarized mitochondria, indicative of impaired fusion-fission events (FIG. 23).

One promising strategy is to reduce the load of diseased mitochondria to a sub-threshold (FIG. 2B) [45-50]. One component of the proposed studies aims to shift heteroplasmy toward healthy mitochondria by enhancing mitochondrial biogenesis. MELAS patients face a maladaptive response in skeletal muscle cells as well as endothelial and smooth muscle cells of small arteries that almost exclusively favors proliferation of diseased mitochondria [46, 47, 51, 52]. This response participates in the pathogenesis of stroke-like episodes in MELAS patients via an undetermined mechanism, possibly involving NO titration by increased COX IV activity in diseased mitochondria [5, 53-55]. Although the mechanism responsible for proliferation of diseased mitochondria remains elusive, it is known to bypass PGC-1α, the master regulator of mitochondrial biogenesis. PGC-1α interacts with key transcription factors, such as PPARs, NRF-1, and NRF-2, to stimulate nuclear gene expression and therefore mitochondrial biogenesis and OXPHOS activities [56-63]. Currently, three approaches regulating the PGC1α pathway have proved insufficient: 1) gene therapy overexpressing PGC-1α improves the OXPHOS capacity in cybrid models and in skeletal muscle of animal models, but gene therapy for mitochondrial diseases is not yet feasible [62]; 2) pharmacological use of the PGC-1α agonist bezafibrate had a limited effect on the mitochondrial mass in most mitochondrial encephalomyopathy mouse models due to insufficient induction of mitochondrial biogenesis [64-70]; and 3) ketogenic diet boosts mitochondrial biogenesis and ATP levels in animal models and reduces the number of mutant mtDNAs in cybrid models, but it is too severe for long-term adherence by patients [71-74]. In addition to this maladaptive response, MELAS fibroblasts have overall less mitochondrial mass than healthy fibroblasts (FIG. 23). Thus, we asked which pharmacological agents could mimic the ketogenic diet and boost biogenesis of functional mitochondrial mass.

The novel pharmaco-epigenomic strategy described herein takes advantage of the dual properties of butyrates. As short chain fatty acids, they can freely diffuse in mitochondria to boost ATP output, while as histone deacetylase inhibitors (HDACis), they act in the nucleus to modulate gene expression via histone acetylation (FIG. 3A). Here, it was discovered that mitochondria respond favorably to butyrate-mediated reprogramming: butyrates reversed the deficits in mitochondrial mass and bioenergetic capacity in MELAS fibroblasts (FIG. 23). Thus, we propose to elucidate the mechanisms by which butyrates augment the functional mitochondrial mass and the bioenergetic capacity in MELAS fibroblasts from a cohort of patients.

(b) Innovation: The studies explore a novel therapeutic approach for MELAS—and more broadly for other mitochondrial disorders—based on the conceptual innovation of using butyrates to rectify mitochondrial dysfunction. The approach has three unique facets: 1) using skin fibroblasts from MELAS patients as an "ex vivo cellular system", high throughput genomics and bioinformatics with pharmaco-epigenomics I used to unravel how the nuclear genome contributes to mitochondrial pathology; 2) the innovative pharmacological approach synergizes key mitochondrial-nuclear crosstalk by generating mitochondrial acetyl-CoA and ATP, both vital for epigenetic modulation of nuclear gene expression and mitochondrial physiology (FIG. 3A); and 3) our striking preliminary results show that butyrates rescue the mitochondrial phenotype in MELAS fibroblasts (FIG. 23). The proposed studies fill the urgent need for a pharmacological way to induce a coupled, robust, and safe mitochondrial biogenic and metabolic response to mitigate the energy deficit in MELAS patients. Our studies will also advance our understanding of the molecular pathogenesis of these disorders.

(c) Approach: The novel pharmacological strategy will be tested using skin fibroblasts from MELAS patients, as MELAS animal models have not been generated due to polyploidy of the mt genome, heteroplasmic load, and influence of the nuclear background on MELAS phenotypic variability [46, 75-78]. Patient fibroblasts are the most suitable system to investigate the therapeutic potential of the butyrates NaBt, tributyrin (TBN), and pivaloyloxymethyl butyrate (AN9) within the context of the patient's nuclear background and heteroplasmy [79, 80]. Valproic acid was excluded due to its propensity to worsen seizures in patients [81]. In future studies, MELAS fibroblasts will be reprogrammed to induced pluripotent stem cells for differentiation into somatic cells [82].

(c-1) Preliminary Results: Clinical safety. Butyrates are well tolerated in humans and are used to treat sickle cell anemia, thalassemia, and more recently, spinal muscular atrophy in clinical trials [83-88]. They are naturally produced in the colon at high concentration (20 mM) where they epigenetically modulate energy metabolism [89]. Despite their potency in the mM range, butyrates display low toxicity in contrast to the high toxicity of hydroxamate-based HDACis, even in their nM range [90, 91]. It was found that the hydroxamates trichostatin A and vorinostat induce apoptosis of MELAS fibroblasts. The butyrates TBN and AN9 show enhanced potency due to improved delivery efficiency and the number of butyric acid molecules upon cleavage by intracellular lipases [92]. AN9, which acts faster than NaBt, exhibits low toxicity, increased cell membrane permeability, and intracellular delivery of butyric acid molecules [93]. Due to its enhanced in vivo potency in the μM range, AN9 is orally administered with low toxicity at pharmacological concentrations 140 times lower than NaBt [93-95]. TBN is more potent than NaBt due to its cleavage into three molecules of butyric acid [91]. A concentration up to 2 mM of TBN is pharmacologically attainable via oral administration without toxicity or side effects [96, 97].

Butyrates easily cross the blood-brain barrier and induce differentiation of embryonic or adult progenitors into neurons through the NeuroD members, such as NeuroD6 [98, 99]. In mouse models of neurodegenerative diseases and ischemia/stroke, NaBt stimulates neurogenesis, enhances synaptic plasticity and memory, while preventing neuronal death—processes in which mitochondria play a crucial role [100-107]. This is particularly relevant given the symptoms of stroke-like episodes, seizures, and dementia in MELAS patients. Chemoproteomic profiling and genetic-based studies revealed that NaBt targets a discrete subset of genes (2-5%) via the HDAC1-3 enzymes [108-114]. Recent genome-wide microarray analysis using MELAS fibroblasts confirms NaBt's limited off-target effect, with only 5% of nuclear genes significantly regulated.

Experimental paradigms. These were: 1) E17.5 differentiating hippocampal neurons expressing NeuroD6 [115-117]; 2) our PC12-NeuroD6 neuronal cell line recapitulating the early stages of differentiation [118-120]; 3) E12.5 timed-pregnant dams treated intraperitoneally with NaBt (1.2 g/Kg) or PBS; and 4) cultured primary skin fibroblasts isolated from two MELAS patients and a healthy subject.

Experimental approaches. Five distinct molecular tools were used to investigate mitochondrial biogenesis: 1) the mitochondrial-specific dyes, MitoTracker® Green (MTG) and MitoTracker® Red (MTR); 2) the mito-GFP or mito-dsRed vector to fluorescently label mitochondria; 3) antibodies against mtDNA, COXVα, or SOD2; 4) the fluorescent PicoGreen® dye labeling mtDNA; and 5) quantitative PCR to determine mtDNA copy number. Dose-dependent studies on healthy and MELAS fibroblasts to determine the optimal safe concentrations of NaBt (2.5 mM), TBN (1.5 mM), and AN9 (300 µM) for eliciting maximal mitochondrial biogenesis without cellular toxicity after three days of treatment were performed.

Figures 20A, 20B, 20C, 20D, 20E, 20F:
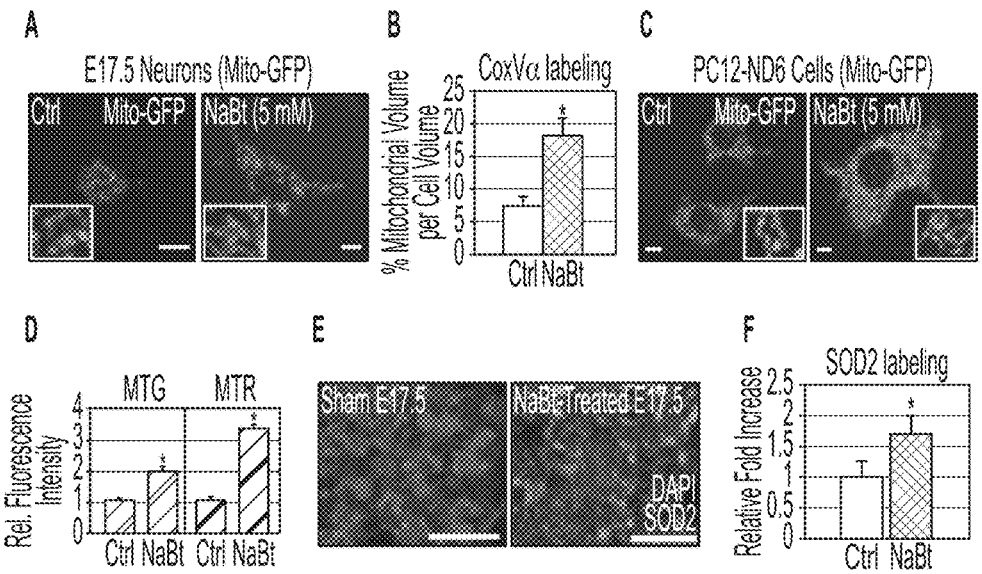
FIG. 20A-20F are images from microscopy and graphs showing that NaBt increases mitochondrial mass. (A) Live cell confocal microscopy of E17.5 hippocampal neurons; high magnification in inset; scale bar=5 (B) Quantitative analysis of the mitochondrial biomass in E17.5 neurons using an anti-CoxVα antibody; *p<0.001. (C) Live cell confocal microscopy of PC12-ND6 cells; high magnification in inset; scale bar=5 (D) Flow cytometric analysis of mitochondrial mass; *p<0.001. (E) Confocal microscopy of E17.5 brains from E12.5 pregnant dams treated with PBS (sham) or NaBt; scale bar=20 μm. (F) Quantitative analysis of mitochondrial mass; *p<0.001.

NaBt increases the mitochondrial biomass of neuronal cells in vitro and in vivo. To investigate NaBt's effect on mitochondrial mass, E17.5 hippocampal neurons and PC12-ND6 cells were transfected with the mito-GFP vector, then exposed them to various NaBt concentrations. Similar results were obtained when neuronal cells were treated for three days with NaBt (2.5 mM) or two days with NaBt (5 mM). Both types of neuronal cells showed increased mitochondrial mass (FIG. 20A, C). Quantitative immunohistochemistry using stacked confocal images and antibodies against COXVα and tubulin revealed mitochondria making up 7% of the cell volume in control and 18% in NaBt-treated E17.5 neurons (FIG. 20B). Flow cytometric analysis using MTG- or MTR-labeled cells corroborated the NaBt-mediated increase in mitochondrial mass (FIG. 20D). While MTG staining showed a two-fold increase in mitochondrial mass, MTR staining revealed an accentuated increase in fluorescence intensity (3.5-fold), suggesting enhanced mitochondrial membrane potential ($\Delta_{\psi m}$) in keeping with the elongated mitochondrial morphology characteristics of bioenergetic mitochondria (FIG. 20A, C, D). Using E12.5 pregnant dams treated intraperitoneally with NaBt or PBS, it was observed that NaBt increased the in vivo mitochondrial mass of E17.5 neurons 1.6-fold (FIG. 20E, F).

Figures 21A, 21B, 21C:
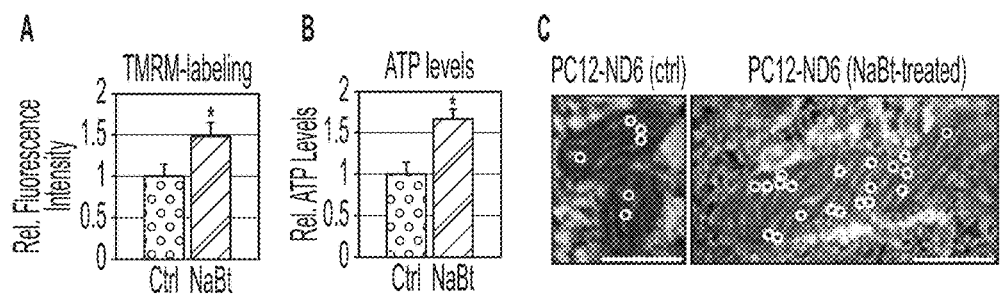
FIG. 21A-21C are images from microscopy and graphs showing that NaBt enhances mitochondrial bioenergetics. (A) Flow cytometric analysis of $\Delta_{\psi m}$; *p<0.001. (B) ATP levels in live cells using a $Mg^{2+}$-based assay; *p<0.001. (C) Electron microscopy of mitochondria in control and NaBt-treated cells; scale bar=200 nm.

NaBt increases mitochondrial membrane potential ($\Delta_{\psi m}$) and ATP levels. MTR-based data raised the question: could NaBt also enhance mitochondrial bioenergetics? $\Delta_{\psi m}$ was assessed by live cell confocal microscopy and flow cytometry using the TMRM dye, which accumulates in the mitochondrial matrix in a $\Delta_{\psi m}$-dependent fashion [40]. A 1.5-fold increase was observed in $\Delta_{\psi m}$ in NaBt-treated cells (FIG. 21A). To test whether enhanced $\Delta_{\psi m}$ led to increased ATP output, ATP levels were monitored using the live cell $Mg^{2+}$-based ATP assay, which is compatible with the TMRM dye, allowing simultaneous recordings [42, 44, 78]. A 1.6-fold increase in ATP levels was observed in NaBt-treated cells (FIG. 21B), in line with our MTR- and TMRM-based findings and the elongated mitochondrial morphology. Electron microscopy confirmed this micro-architectural change with increased numbers of elongated cristae carrying the OXPHOS system and mtDNA foci, indicating enhanced bioenergetic capacity, mitochondrial biogenesis, and mtDNA replication (FIG. 21C).

Figures 22A, 22B, 22C, 22D:
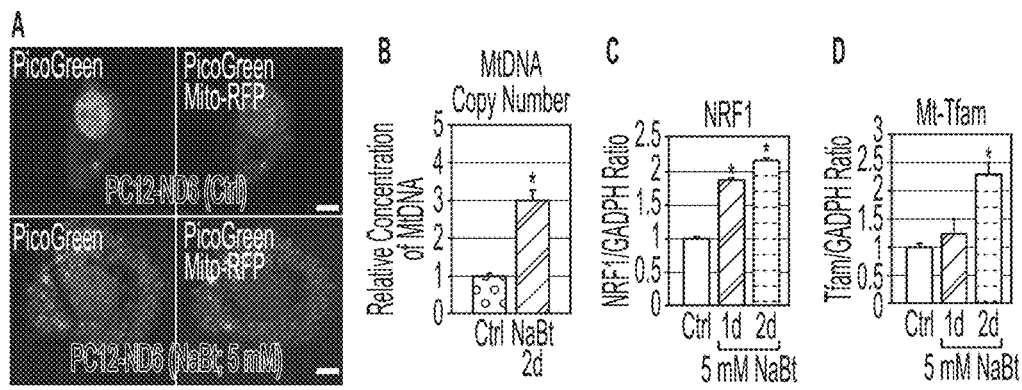
FIG. 22A-22D are images from microscopy and graphs showing that NaBt promotes mtDNA replication via the NRF-1/Tfam axis. (A) Confocal analysis of mtDNA foci; scale bar=5 (B) Quantitative analysis of mtDNA copy number by PCR; *p<0.001. (C, D) Quantitative immunoblot analysis of NRF-1 and Tfam; *p<0.001.

NaBt enhances mtDNA replication via the PGC1α-mediated NRF-1/Tfam axis. It was investigated whether NaBt enhanced mtDNA replication using the PicoGreen® dye to label mtDNA [121-123]. PC12-ND6 cells were transfected with the mito-dsRed vector prior to NaBt treatment followed by PicoGreen® staining. Live cell confocal microscopy revealed an increased number of mtDNA foci in treated cells (FIG. 22A), which was confirmed by quantitative PCR (FIG. 22B). To corroborate enhanced mitochondrial biogenesis, two key target genes of PGC1α were examined, the NRF-1 transcription factor and its direct target gene Tfam, both essential for mitochondrial biogenesis [124-126]. NRF-1 expression increased on day 1 of NaBt treatment followed by induced Tfam expression on day 2 (FIG. 22C, D). These findings confirm the NaBt-mediated modulation of mitochondrial biogenesis and mtDNA replication in neuronal cells.

Figures 23A, 23B, 23C:
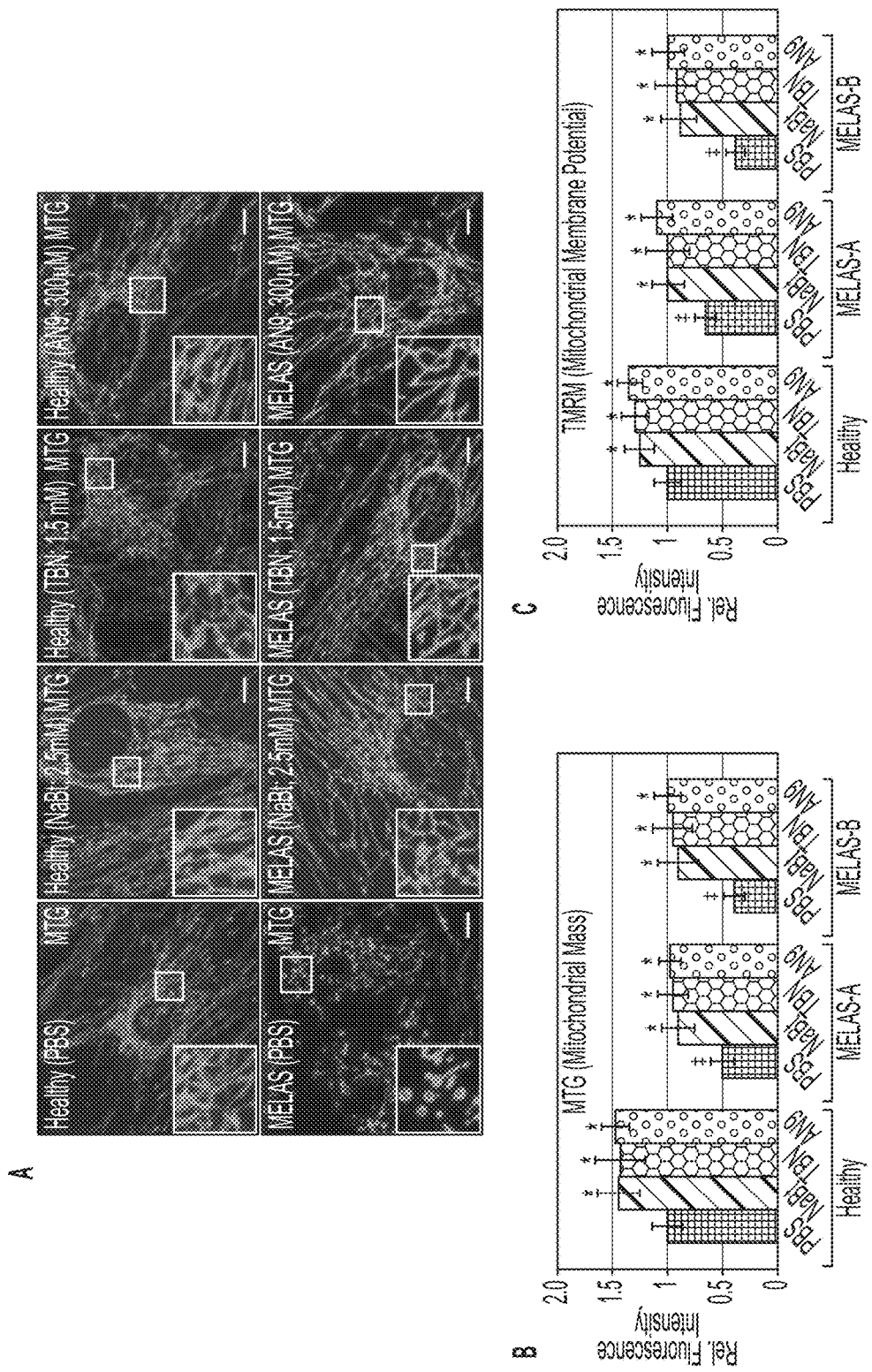
FIG. 23A-23C are images from microscopy and graphs showing that butyrates rescue the mitochondrial phenotype in MELAS fibroblasts. (A) Confocal analysis of healthy and MELAS fibroblasts treated as indicated and labeled with the MTG dye; scale bar=10 (B) Analysis of the mitochondrial mass; n=3 (60 cells per experiment; ‡p<0.05, unpaired T-test *p<0.05, paired T-test). (C) Analysis of $\Delta_{\psi m}$ (‡p<0.05, unpaired T-test; *p<0.05, paired T-test).

Butyrates rescue the mitochondrial mass, morphology, networking, and membrane potential in MELAS fibroblasts. Skin fibroblasts from two MELAS patients and from a healthy subject as a control were used. Dose-dependent analyses of butyrates was performed to determine their best concentrations for eliciting an optimal mitochondrial response without cellular toxicity. Healthy and MELAS fibroblasts were treated with PBS, NaBt (2.5 mM), TBN (1.5 mM), or AN9 (300 µM) for three days before labeling with the MTG dye for live cell confocal analysis. PBS-treated MELAS fibroblasts exhibited reduced mitochondrial mass, mitochondria with fragmented and swollen morphology, as well as abnormal mitochondrial networking, compared to PBS-treated healthy fibroblasts (FIG. 23A). A three-day exposure to NaBt, TBN, or AN9 restored normal mitochondrial mass, morphology, and networking in MELAS fibroblasts (FIG. 23A, B). Morphometric analysis using Image J revealed that butyrates increased the percent of connected and elongated mitochondria from 27±6% to 85±7%, similar to that of PBS-treated healthy fibroblasts. Using the TMRM dye, it was observed that PBS-treated MELAS fibroblasts displayed a lower mitochondrial membrane potential ($\Delta_{\psi m}$) compared to PBS-treated healthy fibroblasts (FIG. 23C). Thus, MELAS fibroblasts were treated with the butyrates before TMRM labeling and it was found that they restored normal levels of $\Delta_{\psi m}$; this confirms restoration of the mitochondrial network, a $\Delta_{\psi m}$-dependent process (FIG. 23C). The duration of this rescue was probed by withdrawing butyrates from the medium and found that the rescued mitochondrial phenotype (mass, networking, and $\Delta_{\psi m}$) was kept up to ten days.

(c-2) Specific Aims: It is hypothesized that the butyrates NaBt, TBN, and/or AN9 can augment the functional mitochondrial mass in skin fibroblasts from a cohort of 20 MELAS patients. Fibroblasts from this number of patients, each with different nuclear backgrounds and heteroplasmic loads, will ensure our findings extend beyond a case study into a statistically sound and broadly applicable report.

Aim 1: Determine how butyrates reduce the burden of diseased mitochondria in MELAS fibroblasts. Rationale: The preliminary data show that mitochondria in MELAS fibroblasts responded favorably to butyrate-mediated reprogramming, leading to a powerful recovery of the mitochondrial phenotype in terms of mass, morphology, and networking activity (FIG. 23). These findings are consistent with the Affymetrix genome-wide microarray data from NaBt-treated MELAS fibroblasts, which indicate increased expression levels of nuclear genes involved in mitochondrial morphology and fusion-fission events. Based on the collective data, it is hypothesized that the three butyrates, NaBt, TBN, and AN9 mitigate the mitochondrial MELAS phenotype via: 1) enhanced mitochondrial biogenesis; 2) upregulation of key nuclear-encoded regulators; and 3) a heteroplasmic shift in favor of functional mitochondria. This hypothesis is supported by the effect of ketogenic bodies on reducing the proportion of mutant mtDNAs in cybrid models bearing mtDNA deletions [72]. The ketogenic diet boosts mitochondrial biogenesis in animal models and eases some symptoms in MRD patients [69, 73, 74].

Experimental Approach: 12 of 20 MELAS patients have been recruited and skin fibroblasts from two healthy subjects are in possession. Patients are being recruited at our affiliated Children's National Medical Center (CMNC) under the leadership of Dr. Batshaw, Chief Academic Officer and Dr. Guay-Woodford, Director of the Clinical and Translational Science Institute (see letters). Our collaborator, Dr. Gropman (see letter), a pediatrician neurologist at CNMC specializing in mitochondrial disorders, will obtain informed consent according to our IRB protocol and will perform the skin biopsies. She is affiliated with the NIH Office of Rare Diseases Research, the North American Mitochondrial Disease Consortium (NAMDC), and the United Mitochondrial Disease Foundation (UMDF), where she serves as a member of the Advisory Board (see letter from UMDF CEO, Mr. Mohan). Only fibroblasts cultured below ten passages will be used. Dose-dependent analyses will be done on fibroblasts from each patient, as in our preliminary studies. We will perform the following assays after three days of butyrate exposure and after five and ten days following drug withdrawal:

Quantitative analysis of the mitochondrial mass and networking: Mitochondrial mass will be quantified by: 1) live cell confocal microscopy, using stacked images of fibroblasts labeled with the MTG dye prior to exposure to PBS or the butyrates NaBt, TBN, and AN9 (FIG. 23); and 2) flow cytometry (FIG. 20). Morphometric analysis will be performed to quantify mitochondrial connectivity and morphology using Image J. We have used these approaches in our preliminary and published studies [42-44].

Quantitative analysis of mtDNA content and replication: mtDNA replication will be assessed by: 1) quantifying mtDNA copy numbers by qPCR (FIG. 22); 2) labeling mt-DNA with PicoGreen® (FIG. 22); and 3) monitoring mtDNA replication using the thymidine analog EdU. For real-time qPCR, PCR primers will be designed for the mt-CO1 gene and the nuclear Ndufv1 gene using the revised Cambridge reference sequence of human mtDNA (NC 012920) [MITOMAP, 127, 128]. Quantification of PicoGreen®-labeled mtDNA will be performed using stacked images from live cell confocal microscopy and Volocity™ software (FIG. 22). mtDNA replication will be analyzed using EdU labeling due to its high sensitivity and compatibility with immunocytochemistry [102]; this will allow discrimination between biogenesis of healthy and diseased mitochondria upon butyrate treatment using antibodies against ND3 or ND6, the mitochondrial-encoded subunits of complex I, both affected in MELAS patients (FIG. 1) [129].

Quantitative immunoblot analysis of key mitochondrial biogenic regulators: Four central regulators of mitochondrial biogenesis will be analyzed: 1) PGC-1α; 2) NRF-1 [122]; 3) NRF-1's direct target gene Tfam, a critical modulator of mtDNA copy number [124]; and 4) NRF-2, another determinant of TFAM expression [126]. Results will be quantified using the LI-COR Technology (FIG. 22).

Quantitative analysis of heteroplasmic shift by PCR and restriction fragment length polymorphism (PCR-RFLP): The relative proportions of WT and mutant mtDNAs will be analyzed by PCR-RFLP analysis using the last cycle hot PCR approach and PCR primers to amplify the mtDNA at the 3243 MELAS position, which generates an HaeIII polymorphism [129, 130].

Feasibility, Predicted Results, Statistical Analysis, and Potential Problems: Since these techniques are established in the laboratory, the experiments of this Aim should be relatively straightforward. Given the preliminary results, it is predicted that one or more of the three butyrates will shift the inter-mitochondrial heteroplasmy toward healthy mitochondria in several nuclear backgrounds.

Aim 2: Determine how butyrates maximize ATP output in MELAS fibroblasts. Rationale: The energy deficit, the main culprit of MELAS, is in fact a therapeutically attractive target to alleviate symptoms in patients. It was observed that NaBt influences structural determinants of mitochondria, such as morphology and density of cristae, while enhancing $\Delta_{\psi m}$ and ATP levels in neuronal cells (FIG. 20, 21). In MELAS fibroblasts, all three butyrates rescued $\Delta_{\psi m}$ to levels similar to those of healthy fibroblasts (FIG. 23). This is concordant with the Ingenuity® pathway analysis performed on the Affymetrix-based microarray data that revealed an enriched OXPHOS pathway (p-value of 5.82E-05) in NaBt-treated MELAS fibroblasts. The fact that butyrates, as short chain fatty acids, are substrates for fatty acid oxidation (FAO) [131] is therapeutically advantageous, as FAO favors the activity of the unaltered complex II, thereby bypassing the deficient complex I (FIG. 1). Thus, it will be investigated how butyrates augment the bioenergetic capacity of MELAS fibroblasts.

Experimental Approach: It will be assessed how NaBt, TBN, and AN9 optimize the bioenergetic output by:

Increasing $\Delta_{\psi m}$ and ATP levels: $\Delta_{\psi m}$ in PBS- or butyrate-treated fibroblasts from healthy and MELAS subjects by live cell confocal microscopy, using the ratiometric dye JC-10 (4 μM), as described in a recent study will be assessed. This ratiometric analysis will quantify the inter-mitochondrial heteroplasmy in terms of $\Delta_{\psi m}$, as reported in cybrid cells bearing the human MELAS mutation [33]. A heat map of $\Delta_{\psi m}$ variations will be generated using Volocity™ software, as shown in the published studies [132]. To determine the impact of butyrates on ATP output (FIG. 1), we will measure ATP levels and the ATP/AMP ratio—the cellular energy index central to mitochondrial-nuclear crosstalk—using commercial bioluminescence assays. Finally, qPCR and immunoblot analyses will be used to validate Affymetrix-based microarray data showing increased expression of 30 OXPHOS genes encoding subunits of complexes II, III, IV, and V (minimum 1.5-fold, p<0.05) in NaBt-treated MELAS fibroblasts.

Bypassing the deficient OXPHOS complex I via increased activity of downstream OXPHOS complexes: Enzymatic activity of the five OXPHOS complexes will be measured using cell lysates instead of mitochondrial-enriched fractions, as defective mitochondria are more fragile and may be damaged during fractionation [133, 134]. Fully intact and functionally active complexes will be isolated by immuno-capturation prior to a colorimetric analysis of their activity using commercial assays.

Favoring a metabolic shift toward FAO to boost ATP output: Following the FAO parameters will be the focus: 1) Flavin Adenine Dinucleotide (FAD), a direct readout of FAO, resulting from oxidation of FADH2 via complex II (FIG. 2), using a commercial colorimetric assay; 2) FGF21, a potent inducer of FAO modulated by NaBt, by immunoblot analysis [135]; and 3) ten upregulated genes in NaBt-treated MELAS fibroblasts known to promote FAO and revealed by the microarray analysis.

Feasibility, Predicted Results, Statistical Analysis, and Potential Problems: Since the techniques are established in the laboratory, there are no major problems foreseen with these experiments. It is anticipated that at least one of the three butyrates will stimulate the bioenergetic capacity of MELAS fibroblasts via a combination of metabolic shift, increased $\Delta_{\psi m}$, and activity of OXPHOS complexes. Statistical analyses will be conducted as in Aim 1. Given that MELAS patients have different nuclear backgrounds and heteroplasmic loads, the strengths of the butyrate responses may vary, posing a potential statistical problem. However, the statistical analysis using a one-sample T-test (two sided) of the butyrate-mediated rescue of the mitochondrial mass of two MELAS patients' fibroblasts showed that this could achieve more than 85% power with just 12 patients.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of treating a subject with a disease or disorder associated with a mitochondrial deficit, comprising:
   determining at least one of a type or degree of said mitochondrial deficit in said subject; and
   administering an effective amount of a butyrate compound to said subject based at least partially on said determining so as to promote Adenosine triphosphate (ATP) production in said subject;
   wherein said butyrate compound is selected from the group of butyrate compounds consisting of sodium butyrate, 1,3-Di(butanoyloxy)propan-2-yl butanoate and pivaloyloxym ethyl butyrate;
   wherein said disease or disorder is Mitochondrial Encephalopathy with Lactic Acidosis and Stroke-like episodes (MELAS), Myoclonic Epilepsy with Ragged-Red Fibers (MERFF), or a mitochondrial respiratory disorder with a deficit in ATP levels due to a genetic mutation in a mitochondrial or nuclear genome.

2. The method of claim 1, wherein said administering an amount of said butyrate compound results in synergizing a mitochondrial-nuclear crosstalk by promoting nuclear reprogramming and mitochondrial metabolic reprogramming.

3. The method of claim 2, wherein said administering an amount of said butyrate compound results in an increase in mitochondrial mass and biogenesis.

4. The method of claim 2, wherein said administering an amount of said butyrate compound results in increased mitochondrial membrane potential and bioenergetics.

5. The method of claim 1, wherein said administering an amount of said butyrate compound results in a decrease of diseased mitochondria.

6. The method of claim 1, wherein said butyrate compound is administered in an amount of about 150 mg/Kg/day to about 500 mg/Kg/day.

7. The method of claim 1, wherein said butyrate compound is administered for at least 3 days.

8. The method of claim 7, further comprising observing a resting period following administration of said butyrate compound and prior to administration of a subsequent dose of said butyrate compound.

9. The method of claim 1, wherein said butyrate compound is administered orally, intravenously, or by injection.

* * * * *